US006426364B1

(12) United States Patent
Egle et al.

(10) Patent No.: US 6,426,364 B1
(45) Date of Patent: Jul. 30, 2002

(54) DIARYL-ENYNES

(75) Inventors: Ian Egle, Mississauga; Jennifer Frey, Brampton; Methvin Isaac, Etobicoke, all of (CA)

(73) Assignee: NPS Allelix Corp., Ontario (CA)

( * ) Notice: Subject to any disclaimer, the term of this patent is extended or adjusted under 35 U.S.C. 154(b) by 50 days.

(21) Appl. No.: 09/704,225

(22) Filed: Nov. 1, 2000

Related U.S. Application Data
(60) Provisional application No. 60/162,986, filed on Nov. 1, 1999.

(51) Int. Cl.[7] .................... A61K 31/198; A61P 25/18; C07D 317/60
(52) U.S. Cl. .................... 514/465; 514/367; 549/444; 562/426; 562/443; 562/444; 562/449; 560/9; 560/17; 560/21; 560/38
(58) Field of Search .................... 549/444; 562/443; 514/465

(56) References Cited

PUBLICATIONS

Greenhill, Chemical Abstracts, vol. 73, No. 425, 067 (1976).*

* cited by examiner

Primary Examiner—Robert W. Ramsuer
(74) Attorney, Agent, or Firm—Dechert

(57) ABSTRACT

Provided, among other things, is a compound of Formula I:

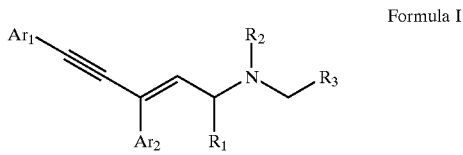

Formula I wherein:
  $Ar_1$ and $Ar_2$ are independently selected aryl groups, optionally substituted with up to five substituents independently selected from the group consisting of
    alkyl, alkoxy, cycloalkyl, cycloalkyloxy, heterocycloalkyl, heterocycloalkyloxy, alkanoyl, thioalkyl, aralkyl, aralkyloxy, aryloxyalkyl, aryloxyalkoxy, cycloalkyl-substituted alkyl, cycloalkyloxy-substituted alkyl, cycloalkyl-substituted alkoxy, cycloalkyloxy-substituted alkoxy, heterocycloalkyl-substituted alkyl, heterocycloalkyloxy-substituted alkyl, heterocycloalkyl-substituted alkoxy, heterocycloalkyloxy-substituted alkoxy, thioaryl, aralkylthio, thioarylalkyl, aralkylthioalkyl, halo, $NO_2$, $CF_3$, CN, OH, alkylenedioxy, $SO_2NRR'$, $NRR'$, $CO_2R$ (where R and R' are independently selected from the group consisting of H and alkyl), and a second aryl group, which may be substituted as above;
  $R_1$ is selected from the group consisting of H and alkyl;
  $R_2$ is selected from the group consisting of H, alkyl and benzyl;
  $R_3$ is selected from the group consisting of $CO_2R$, $CONRR'$, $CONH(OH)$, $COSR$, $SO_2NRR'$, $PO(OR)(OR')$ and tetrazolyl, wherein R and R' are independently selected from the group consisting of H and alkyl;
and a salt, solvate or hydrate thereof.

31 Claims, No Drawings

DIARYL-ENYNES

This application claims the benifit of Provisional Application No. 60/162,986, filed Nov. 1, 1999.

The present invention relates to a class of diaryl-enynes, to pharmaceutical compositions containing them and to methods of treating neurological and neuropsychiatric disorders using such compounds.

BACKGROUND OF THE INVENTION

Synaptic transmission is a complex form of intercellular communication that involves a considerable array of specialized structures in both the pre- and post-synaptic terminal and surrounding glial cells (Kanner and Schuldiner, *CRC Critical Reviews in Biochemistry*, 22, 1987:1032). Transporters sequester neurotransmitter from the synapse, thereby regulating the concentration of neurotransmitter in the synapse, as well as its duration therein, which together influence the magnitude of synaptic transmission. Further, by preventing the spread of transmitter to neighbouring synapses, transporters maintain the fidelity of synaptic transmission. Lastly, by sequestering released transmitter into the presynaptic terminal, transporters allow for transmitter reutilization.

Neurotransmitter transport is dependent upon extracellular sodium and the voltage difference across the membrane; under conditions of intense neuronal firing, as, for example, during a seizure, transporters can function in reverse, releasing neurotransmitter in a calcium-independent non-exocytotic manner (Attwell et al., *Neuron*, 11, 1993:401–407). Pharmacologic modulation of neurotransmitter transporters thus provides a means for modifying synaptic activity, which provides useful therapy for the treatment of neurological and psychiatric disturbances.

The amino acid glycine is a major neurotransmitter in the mammalian central nervous system, functioning at both inhibitory and excitatory synapses. By nervous system, both the central and peripheral portions of the nervous system are intended. These distinct functions of glycine are mediated by two different types of receptor, each of which is associated with a different class of glycine transporter. The inhibitory actions of glycine are mediated by glycine receptors that are sensitive to the convulsant alkaloid strychnine, and are thus referred to as "strychnine-sensitive". Such receptors contain an intrinsic chloride channel that is opened upon binding of glycine to the receptor; by increasing chloride conductance, the threshold for firing of an action potential is increased. Strychnine-sensitive glycine receptors are found predominantly in the spinal cord and brainstem, and pharmacological agents that enhance the activation of such receptors will thus increase inhibitory neurotransmission in these regions.

Glycine also functions in excitatory transmission by modulating the actions of glutamate, the major excitatory neurotransmitter in the central nervous system (Johnson and Ascher, *Nature*, 325, 1987:529–531; Fletcher et al., *Glycine Transmission*, Otterson and Storm-Mathisen, eds., 1990:193–219). Specifically, glycine is an obligatory co-agonist at the class of glutamate receptor termed N-methyl-D-aspartate (NMDA) receptor. Activation of NMDA receptors increases sodium and calcium conductance, which depolarizes the neuron, thereby increasing the likelihood that it will fire an action potential.

NMDA receptors in the hippocampal region of the brain play an important role in a model of synaptic plasticity known as long-term potentiation (LTP), which is integral in certain types of learning and memory (Hebb, D. O (1949) *The Organization of Behavior;* Wiley, N.Y.; Bliss and Collingridge (1993) *Nature* 361: 31–39; Morris et al. (1986) *Nature* 319: 774–776). Enhanced expression of selected NMDA receptor sub-units in transgenic mice results in increased NMDA-receptor-mediated currents, enhanced LTP, and better performance in some tests of learning and memory (Tang et al. (999) *Nature* 401: 63).

Conversely, decreased expression of selected NMDA receptor sub-units in transgenic mice produces behaviors similar to pharmacologically-induced animal models of schizophrenia, including increased locomotion, increased stereotypy, and deficits in social/sexual interactions (Mohn et al. (1999) *Cell* 98:427–436). These aberrant behaviors can be ameliorated using the antipsychotics haloperidol and clozapine.

NMDA receptors are widely distributed throughout the brain, with a particularly high density in the cerebral cortex and hippocampal formation.

Molecular cloning has revealed the existence in mammalian brains two classes of glycine transporters, termed GlyT-1 and GlyT-2. GlyT-1 is found throughout the brain and spinal cord, and it has been suggested that its distribution corresponds to that of glutamatergic pathways and NMDA receptors (Smith, et al., *Neuron*, 8, 1992:927–935). Molecular cloning has further revealed the existence of three variants of GlyT-1, termed GlyT-1a, GlyT-1b and GlyT-1c. Two of these variants (1a and 1b) are found in rodents, each of which displays a unique distribution in the brain and peripheral tissues (Borowsky et al., *Neuron*, 10, 1993:851–863; Adams et al., *J. Neuroscience*, 15, 1995:2524–2532). The third variant, 1c, has only been detected in human tissues (Kim, et al., *Molecular Pharmacology*, 45, 1994:608–617). These variants arise by differential splicing and exon usage, and differ in their N-terminal regions. GlyT-2, in contrast, is found predominantly in the brain stem and spinal cord, and its distribution corresponds closely to that of strychnine-sensitive glycine receptors (Liu et al., *J. Biological Chemistry*, 268, 1993:22802–22808; Jursky and Nelson, *J. Neurochemistry*, 64, 1995:1026–1033). Another distinguishing feature of glycine transport mediated by GlyT-2 is that it is not inhibited by sarcosine as is the case for glycine transport mediated by GlyT-1. These data are consistent with the view that, by regulating the synaptic levels of glycine, GlyT-1 and GlyT-2 selectively influence the activity of NMDA receptors and strychnine-sensitive glycine receptors, respectively.

Compounds which inhibit or activate glycine transporters would thus be expected to alter receptor function and, thus, provide therapeutic benefits in a variety of disease states.

For example, compounds which inhibit GlyT-1 mediated glycine transport will increase glycine concentrations at NMDA receptors, which receptors are located in the forebrain, among other locations. This concentration increase elevates the activity of NMDA receptors, thereby alleviating schizophrenia and enhancing cognitive function. Alternatively, compounds that interact directly with the glycine receptor component of the NMDA receptor can have the same or similar effects as increasing or decreasing the availability of extracellular glycine caused by inhibiting or enhancing GlyT-1 activity, respectively. See, for example, Pitkänen et al., *Eur. J. Pharmacol.*, 253, 125–129 (1994); Thiels et al., *Neuroscience*, 46, 501–509 (1992); and Kretschmer and Schmidt, *J. Neurosci.*, 16, 1561–1569 (1996).

The present invention provides compounds that affect glycine transport. The invention also provides compositions useful to treat medical conditions for which a glycine transport modulator, and particularly glycine uptake inhibitors, are indicated.

SUMMARY OF THE INVENTION

According to one aspect of the invention, there are provided compounds of Formula I:

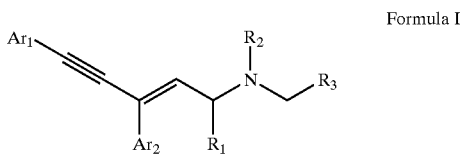

Formula I wherein:
- $Ar_1$ and $Ar_2$ are independently selected aryl groups, optionally substituted with up to five substituents independently selected from the group consisting of alkyl, alkoxy, cycloalkyl, cycloalkyloxy, heterocycloalkyl, heterocycloalkyloxy, alkanoyl, thioalkyl, aralkyl, aralkyloxy, aryloxyalkyl, aryloxyalkoxy, cycloalkyl-substituted alkyl, cycloalkyloxy-substituted alkyl, cycloalkyl-substituted alkoxy, cycloalkyloxy-substituted alkoxy, heterocycloalkyl-substituted alkyl, heterocycloalkyloxy-substituted alkyl heterocycloalkyl-substituted alkoxy, heterocycloalkyloxy-substituted alkoxy, thioaryl, aralkylthio, thioaryl-alky, aralkylthioalkyl, halo, $NO_2$, $CF_3$, CN, OH, alkylenedioxy, $SO_2NRR'$, NRR', $CO_2R$ (where R and R' are independently selected from the group consisting of H and alkyl) and a second aryl group, which may be substituted as above;
- $R_1$ is selected from the group consisting of H and alkyl;
- $R_2$ is selected from the group consisting of H, alkyl and benzyl;
- $R_3$ is selected from the group consisting of $CO_2R$, CONRR', CONH(OH), COSR, $SO_2NRR'$, PO(OR)(OR') and tetrazolyl, wherein R and R' are independently selected from the group consisting of H and alkyl;

and a salt, solvate or hydrate thereof.

It has been found that compounds of Formula I inhibit glycine transport (or reuptake) via the GlyT-1 transporter, or are precursors (for example, pro-drugs) of such compounds and, thus, are useful in the treatment of schizophrenia, as well as other CNS-related disorders such as cognitive dysfunction, dementia (including that related to Alzheimer's disease), attention deficit disorder and depression.

According to another aspect of the invention, there is provided a pharmaceutical composition comprising a compound of Formula I in an amount effective to inhibit glycine transport, and a pharmaceutically acceptable carrier.

In another aspect of the invention there are provided compositions containing the present compounds in amounts for pharmaceutical use to treat medical conditions for which a glycine transport inhibitor is indicated. Preferred are those compositions containing compounds useful in the treatment of medical conditions for which GlyT-1-mediated inhibition of glycine transport is needed, such as the treatment of schizophrenia or cognitive dysfunction.

Definitions

The term aryl as used herein means a monocyclic aromatic group such as phenyl, pyridyl, furyl, thienyl, and the like, or a benzo-fused aromatic group such as naphthyl, indanyl, quinolinyl, fluorenyl and the like.

The term alkyl as used herein means straight- and branched-chain alkyl radicals containing from one to six carbon atoms and includes methyl, ethyl and the like.

The term cycloalkyl as used herein means a carbocyclic ring containing from three to eight carbon atoms and includes cyclopropyl, cyclohexyl and the like. Similarly, the term "cycloalkyloxy" refers to such a carbocycle that is coupled through an oxygen to another group, and includes cyclohexyloxy and the like.

The term heterocycloalkyl as used herein means a three- to eight-membered ring containing up to two heteroatoms selected from the group consisting of N, S and O, and includes piperidinyl, piperazinyl, thiopyranyl and the like. Such rings coupled to another group through an oxygen, such as piperidinyloxy and the like, are referred to as heterocycloalkyloxy groups.

The terms aralkyl, aryloxyalkyl, aralkyloxy and aryloxyalkoxy as used herein refer to an alkyl or alkoxy radical substituted with an aryl or aryloxy group and includes benzyl, phenethyl, benzyloxy, 2-phenoxyethyl and the like. Similarly, the terms cycloalkyl-substituted alkyl, cycloalkyl-substituted alkoxy, heterocycloalkyl-substituted alkyl and heterocycloalkyl-substituted alkoxy mean groups such as 2-cyclohexyl-ethyl and the like. Further, substituents in which an alkyl or alkoxy group is substituted by another group through a bridging oxygen, are groups referred to herein as cycloalkyloxy-substituted alkyl, cycloalkyloxy-substituted alkoxy, heterocycloalkyloxy-substituted alkyl and heterocycloalkyloxy-substituted alkoxy.

The terms alkylene (e.g., —CH2—CH2—), alkenylene (e.g., —CH═CH—) and alkynylene (e.g., —CH≡CH—) as used herein means straight- and branched-chain bivalent radicals containing from one to six carbon atoms, such as methylene, ethylene, vinylene, propenylene and ethynylene.

The terms alkylene (e.g., —CH2—CH2—), alkenylene (e.g., —CH═CH—) and alkynylene (e.g., —CH≡CH—) as used herein means straight- and branched-chain bivalent radicals containing from one to six carbon atoms, such as methylene, ethylene, vinylene, propenylene and ethynylene.

The term alkoxy as used herein means straight- and branched-chain alkoxy radicals containing from one to six carbon atoms and includes methoxy, ethoxy and the like.

The term thioalkyl as used herein means straight- and branched-chain alkyl radicals containing from one to six carbon atoms and includes thiomethyl (CH3—S—), thiopropyl and the like.

The term thioaryl refers to an aryl group that is bridged to another group through a sulfur. Similarly, a thioarylalkyl group is a thioaryl group bridged to another group through an alkylene group. Also, an aralkythio group is an aralkyl group, such as benzyl, which is bridged to another group through a sulfur atom. Further, an arylalkylthioalkyl group is an arylalkyl group that is bridged to another group through a thioalkyl group.

The term alkanoyl as used herein means straight- and branched-chain radicals containing from one to six carbon atoms and includes acetyl, propionyl and the like.

The term halo as used herein means halogen and includes fluoro, chloro, bromo and the like. The term haloalkyl refers to an alkyl group substituted by one or more independently selected halo atoms, such as —CF3. Similarly, the term haloalkoxy refers to an alkoxy group substituted by one or more independently selected halo atoms, such as —OCF3.

The term alkylenedioxy refers to a group of the formula —O—(CH2)n—O—, in which the terminal oxygen typically are fused to atoms on an aryl group to form a bicyclic ring system, and includes methylenedioxy, ethylenedioxy and the like.

The term hetero atom as used herein means atoms other carbon and includes N, S and O.

DETAILED DESCRIPTION AND PREFERRED EMBODIMENTS

The geometry about the double bond of the compounds of Formula I is as drawn. That is, group $Ar_2$ and the carbon atom to which group $R_1$ is attached are cis to each other.

Compounds of Formula I include those in which $Ar_1$ and $Ar_2$ are, independently, optionally-substituted aryl groups.

Substitution sites on rings $Ar_1$ and $Ar_2$ will be limited in practice to the carbon atoms on the ring not bound to the core of the molecule. For example, a benzene ring can be substituted with up to 5 substituents; pyridine and pyran can accommodate up to 4 substituents pyrole furan and thiophene can accommodate up to 3 substituents; imidazole 2 substituents and triazole can accommodate only one substituent.

In embodiments of the invention Arl is an optionally monocyclic aromatic group such as benzene, pyridine, pyran, thiophene, furan, pyrole, imidazole and triazole. $Ar_1$ suitably accomodates 1, 2 or 3 substituents on the aromatic ring and these can be chosen from such groups as alkyl, alkoxy, cycloalkyl, cycloalkyloxy, heterocycloalkyl, heterocycloalkyloxy, alkanoyl, thioalkyl, aralkyl, aralkyloxy, aryloxyalkyl, aryloxyalkoxy, cycloalkyl-substituted alkyl, cycloalkyloxy-substituted alkyl, cycloalkyl-substituted alkoxy, cycloalkyloxy-substituted alkoxy, heterocycloalkyl-substituted alkyl, heterocycloalkyloxy-substituted alkyl heterocycloalkyl-substituted alkoxy, heterocycloalkyloxy-substituted alkoxy, thioaryl, aralkylthio, thioaryl-alky, halo, $NO_2$, $CF_3$, CN, OH, methylenedioxy, ethylenedioxy, $SO_2NRR'$, NRR', $CO_2R$ (where R and R' are independently selected from the group consisting of H and alkyl) or an aryl group optionally substituted as stated above.

In suitable embodiments of the invention, $Ar_1$ is selected from benzene, pyridine, pyran, thiophene, furan and pyrole, optionally substituted with 1, 2 or 3 substituents selected from halo, NO2, CF3, CN, OH, alkyl, alkoxy, aryl, aralkyl, and $R''(X)n$. where n is 0 or 1;X is $CH_2$ or a heteroatom; and R" is H, alkyl or aryl substituted optionally with up to three substituents selected from alkyl, halo, $NO_2$, $CF_3$, CN, OH, $SO_2NRR'$, NRR', and $CO_2R$ (where R and R' are independently selected from the group consisting of H and alkyl).

In particular embodiments, $Ar_1$ is phenyl optionally substituted with 1, 2 or 3 substituents selected from halo, NO2, CF3, CN, OH, and $R''(X)_n$ where n is 0 or 1; X is $CH_2$ O, S, or NR; and R" is H, alkyl or aryl substituted optionally with up to three substituents selected independently from alkyl, halo, $NO_2$, $CF_3$, CN, OH, $SO_2NRR'$, NRR', $CO_2R$ (where R and R' are independently selected from the group consisting of H and alkyl).

In more particular embodiments, $Ar_1$ is phenyl optionally substituted with 1 or 2 substituents selected from alkyl, thioalkyl, alkoxy, halo, haloalkyl, haloalkoxy, substituted or unsubstituted aryl, substituted or unsubstituted aryloxy, and substituted or unsubstituted aralkyl.

In specific embodiments, $Ar_1$ is mono-substituted phenyl where the substituent is located at the 4 position and is selected from methyl, ethyl, n-propyl, i-propyl, n-butyl, 3-furyl, and 3-thienyl.

In other embodiments, $Ar_1$ is an optionally substituted benzofused aromatic group such as naphthalene, quinoline, indole, anthracene, fluorenyl, alkylenedioxyphenyl and the like, where the substituents can be selected from halo, NO2, CF3, CN, OH, alkyl, alkoxy, aryl, aralkyl, and $R''(X)_n$ where n is 0 or 1; X is $CH_2$ or a heteroatom; and R" is H, alkyl or aryl substituted optionally with up to three substituents selected from alkyl, halo, $NO_2$, $CF_3$, CN, OH, $SO_2NRR'$, NRR', $CO_2R$ (where R and R' are independently selected from the group consisting of H and alkyl).

In particular embodiments, $Ar_1$ can be naphthyl, quinolinyl, indanyl, or alkylenedioxyphenyl, optionally substituted with 1 or 2 substituents selected from alkyl, alkoxy, thioalkyl and aryl.

In a specific embodiment, $Ar_1$ is selected from unsubstituted naphthalene and methylenedioxyphenyl.

In other embodiments of the invention, $Ar_2$ is an optionally substituted aryl, where aryl, is a monocyclic aromatic group such as benzene, pyridine, pyran, furan, thiophene, pyrrolidine and the like, or is a benzofused aromatic ring system such as naphthalene, quinoline, indole, anthracene, fluorenyl, alkylenedioxyphenyl and the like. Either 1, 2, or 3 substituents may be present, and these may be independently selected from halo, haloalkyl, alkyl, haloalkoxy, and alkoxy.

In a particular embodiment, A is a monocyclic aromatic ring bearing up to three substituents selected independently from halo, haloalkyl, alkyl, haloalkoxy, and alkoxy. In more particular embodiments, A is selected from mono or di-substituted phenyl, where the substituents are selected from halo, haloalkyl, alkyl, haloalkoxy, and alkoxy.

In specific embodiments, $Ar_2$ is a phenyl group that is either unsubstituted or has one substituent selected from halo and alkoxy.

In more specific embodiments, $Ar_2$ is selected from unsubstituted or mono substituted phenyl, where the substituent is selected from chloro and flouro.

In other embodiments of the invention, $R_3$ is selected from the group consisting of $-CO_2R$, $-CONRR'$, $-CONH(OH)$, $-COSR$, $-SO_2NRR'$, $-PO(OR)(OR')$ and tetrazolyl wherein R and R' are independently selected from the group consisting of H and alkyl.

In particular embodiments, $R_3$ is COOR. In preferred embodiments of the invention, $R_3$ is COOH.

The compounds of Formula I include those in which R1 is selected from the group consisting of H and alkyl. Preferably, $R_1$ is H.

The compounds of Formula I include those in which $R_2$ is selected from the group consisting of H, alkyl and benzyl. Suitably, $R_2$ alkyl; more preferably, $R_2$ is methyl.

In preferred embodiments, compounds of Formula I are those in which $R_1$ is H, $R_2$ is methyl, $R_3$ is COOH. In this context, $Ar_1$ and $Ar_2$ are desirably substituted or unsubstituted phenyl. Preferably, $Ar_1$ is either phenyl or 4-(substituted)-phenyl. When substituted, $Ar_1$ is desirably a 4-(alkyl)-phenyl group, particularly where the alkyl group is a straight-chain alkyl group, including 4-isopropyl-phenyl, 4-ethyl-phenyl, and 4-n-propyl-phenyl. Either in combination therewith or independently thereof, $Ar_2$ is preferably is chloro or fluoro substituted phenyl.

In another preferred embodiment, $R_1$ is H, $R_2$ is methyl, $R_3$ is COOH, $Ar_2$ is unsubstituted phenyl and $Ar_1$ is 4-alkyl substituted phenyl where alkyl is $C_{1-4}$ straight chain.

In another preferred embodiment $R_1$ is H, $R_2$ is methyl, $R_3$ is COOH, $Ar_2$ is 2-chlorophenyl and $Ar_1$ is 4-alkyl phenyl where the alkyl substituent is selected from ethyl and propyl.

In another preferred embodiment of the invention $R_1$ is H, $R_2$ is methyl, $R_3$ is COOH, $Ar_1$ is naphthyl, especially 2-naphthyl, and $Ar_2$ is phenyl.

In yet another preferred embodiment of the invention $R_1$ is H, $R_2$ is methyl, $R_3$ is COOH, $Ar_1$ is 3,4-methylenedioxyphenyl and $Ar_2$ is 3-fluoro-phenyl.

In still another preferred embodiment of the invention $R_1$ is H, $R_2$ is methyl, $R_3$ is COOH, $Ar_2$ is phenyl and $Ar_1$ is an optionally substituted aryl substituted phenyl.

In a more preferred embodiment of the invention $R_1$ is H, $R_2$ is methyl, $R_3$ is COOH, $Ar_2$ is phenyl and $Ar_1$ is phenyl substituted by a 5-membered heteroaryl that is optionally substituted.

In a most preferred embodiment of the invention $R_1$ is H, $R_2$ is methyl, $R_3$ is COOH, $Ar_2$ is phenyl and $Ar_1$ is 4-(3-furyl)phenyl.

Specific compounds of Formula I include:

N-(5-(4-Fluorophenyl)-3-phenyl-2-penten-4-yn-1-yl)-sarcosine
N-(5-(2-Fluorophenyl)-3-phenyl-2-penten-4-yn-1-yl)-sarcosine
N-(5-(2,4-Difluorophenyl)-3-phenyl-2-penten-4-yn-1-yl)-sarcosine
N-(5-(3-Nitrophenyl)-3-phenyl-2-penten-4-yn-1-yl)-sarcosine
N-(5-(4-Nitrophenyl)-3-phenyl-2-penten-4-yn-1-yl)-sarcosine
N-(3-Phenyl-5-(2-thiomethylphenyl)-2-penten-4-yn-1-yl)-sarcosine
N-(5-(4-Chlorophenyl)-3-phenyl-2-penten-4-yn-1-yl)-sarcosine
N-(5-(4-Isopropylphenyl)-3-phenyl-2-penten-4-yn-1-yl)-sarcosine,
N-(5-(3,5-Bis(trifluoromethyl)phenyl)-3-phenyl-2-penten-4-yn-1-yl)-sarcosine
N-(3,5-Diphenyl-2-penten-4-yn-1-yl)-sarcosine
N-(5-(4-diphenyl)-3-phenyl-2-penten-4-yn-1-yl)-sarcosine
N-(5-(4-trifluoromethylphenyl)-3-phenyl-2-penten-4-yn-1-yl)-sarcosine
N-(5-(4-benzylphenyl)-3-phenyl-2-penten-4-yn-1-yl)-sarcosine
N-(5-(4-ethylphenyl)-3-phenyl-2-penten-4-yn-1-yl)-sarcosine
N-(5-(4-"propylphenyl)-3-phenyl-2-penten-4-yn-1-yl)-sarcosine
N-(5-(4-"butylphenyl)-3-phenyl-2-penten-4-yn-1-yl)-sarcosine
N-(5-(4-"pentylphenyl)-3-phenyl-2-penten-4-yn-1-yl)-sarcosine
N-(5-(4-phenoxyphenyl)-3-phenyl-2-penten-4-yn-1-yl)-sarcosine
N-(5-(1-naphthyl)-3-phenyl-2-penten-4-yn-1-yl)-sarcosine
N-(5-(4-methylphenyl)-3-phenyl-2-penten-4-yn-1-yl)-sarcosine
N-(5-(3-isopropylphenyl)-3-phenyl-2-penten-4-yn-1-yl)-sarcosine
N-(5-(2-naphthyl)-3-phenyl-2-penten-4-yn-1-yl)-sarcosine
N-(5-(3,4-dimethylphenyl)-3-phenyl-2-penten-4-yn-1-yl)-sarcosine
N-(5-(2-isopropylphenyl)-3-phenyl-2-penten-4-yn-1-yl)-sarcosine
N-(5-(3,4-methylenedioxyphenyl)-3-phenyl-2-penten-4-yn-1-yl)-sarcosine
N-(5-(4-pyrrolylphenyl)-3-phenyl-2-penten-4-yn-1-yl)-sarcosine
N-(5-(4-trifluoromethoxyphenyl)-3-phenyl-2-penten-4-yn-1-yl)-sarcosine
N-(5-(3,4-dimethoxyphenyl)-3-phenyl-2-penten-4-yn-1-yl)-sarcosine
N-(3-Phenyl-5-(4-thiomethylphenyl)-2-penten-4-yn-1-yl)-sarcosine
N-(5-(4-Methylphenyl)-3-phenyl-2-penten-4-yn-1-yl)-sarcosine
N-(3-Phenyl-5-(3-thiophene)-2-penten-4-yn-1-yl)-sarcosine
N-(3-Phenyl-5-(4-tbutylphenyl)-2-penten-4-yn-1-yl)-sarcosine
N-(5-(4-(3-furyl)-phenyl)-3-phenyl-2-penten-4yn-1-yl)-sarcosine
N-(5-(4-(3-thiophene)-phenyl)-3-phenyl-2-penten-4-yn-1-yl)-sarcosine
N-(5-(4-Isopropylphenyl)-3-(4-(trifluoromethyl)phenyl)-2-penten-4-yn-1-yl)-sarcosine
N-(5-(4-Isopropylphenyl)-3-(4-fluorophenyl)-2-penten-4-yn-1-yl)-sarcosine
N-(5-(4-Isopropylphenyl)-3-(2-fluorophenyl)-2-penten-4-yn-1-yl)-sarcosine
N-(5-(4-t-Butylphenyl)-3-(2-fluorophenyl)-2-penten-4-yn-1-yl)-sarcosine
N-(5-(4-Isopropylphenyl)-3-(4-chlorophenyl)-2-penten-4-yn-1-yl)-sarcosine
N-(5-(4-t-Butylphenyl)-3-(4-chlorophenyl)-2-penten-4-yn-1-yl)-sarcosine
N-(5-(4-Isopropylphenyl)-3-(2-chlorophenyl)-2-penten-4-yn-1-yl)-sarcosine
N-(5-(4-t-Butylphenyl)-3-(2-chlorophenyl)-2-penten-4-yn-1-yl)-sarcosine
N-(5-(4-Isopropylphenyl)-3-(3-fluorophenyl)-2-penten-4-yn-1-yl)-sarcosine
N-(5-(4-Isopropylphenyl)-3-(3-thienyl)-2-penten-4-yn-1-yl)-sarcosine
N-(5-(4-Isopropylphenyl)-3-(4-methoxyphenyl)-2-penten-4-yn-1-yl)-sarcosine
N-(5-(3,4-Methylenedioxyphenyl)-3-(3-fluorophenyl)-2-penten-4-yn-1-yl)-sarcosine
N-(5-(4-Ethylphenyl)-3-(2-chlorophenyl)-2-penten-4-yn-1-yl)-sarcosine
N-(5-(4-Propylphenyl)-3-(2-chlorophenyl)-2-penten-4-yn-1-yl)-sarcosine Compounds of Formula I can be considered to be amino acids or derivatives thereof. Compounds which contain, instead of a carboxylate group, a "carboxylate equivalent" group, such as hydroxamic acids, phosphonic acids, phosphinic acids, sulfonic acids, sulfinic acids, amides or tetrazoles, are also considered embodiments of the present invention.

In another embodiment of the invention, the compound of Formula I is provided in labeled form, such as radiolabeled form (e.g. labeled by incorporation within its structure $^3$H or $^{14}$C or by conjugation to $^{125}$I). In a preferred aspect of the invention, such compounds, which bind preferentially to GlyT-1, can be used to identify GlyT-1 receptor ligands by techniques common in the art. This can be achieved by incubating the receptor or tissue in the presence of a ligand candidate and then incubating the resulting preparation with an equimolar amount of radiolabeled compound of the invention. GlyT-1 receptor ligands are thus revealed as those that significantly occupy the GlyT-1 site and prevent binding of the radiolabeled compound of the present invention. Alternatively, GlyT-1 receptor ligand candidates may be identified by first incubating a radiolabeled form of a compound of the invention then incubating the resulting preparation in the presence of the candidate ligand. A more potent GlyT-1 receptor ligand will, at equimolar concentration, displace the radiolabeled compound of the invention.

Acid addition salts of the compounds of Formula I are most suitably formed from pharmaceutically acceptable acids, and include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of Formula I for laboratory use, or for subsequent conversion to a pharmaceutically acceptable acid addition salt. Also included within the scope of the invention are base addition salts (such as sodium, potassium and ammonium salts), solvates and hydrates of compounds of the invention. Base salts are preferred and sodium and potassium salts are especially preferred.

The conversion of a given compound salt to a desired compound salt is achieved by applying standard techniques, well known to one skilled in the art.

The compounds of the present invention can be prepared by processes analogous to those established in the art. For example, compounds of Formula I are readily prepared by the method shown in Scheme 1, below. Intermediate C was prepared according to the method of Trost (Trost, B. M.; Sorum, M. T.; Chan, C.; Harms, A. E.; Ruther, G. *J. Am. Chem. Soc.* 1997, 119, 698–708; Trost, B. M.; Hachiya, I.; McIntosh, M. C. *Tetrahedron Lett.* 1998, 39, 6445–6448) by coupling an arylpropiolic ester such as A with trimethylsilylacetylene B in the presence of palladium acetate and tris(2,6-dimethoxyphenyl)phosphine. Reduction of the ester to the alcohol, and treatment with N-Bromosuccinimide gave bromide D. Treatment of D with a sarcosine ester (such as tbutyl sarcosine) in the presence of base gave the intermediate sarcosine derivative E. Removal of the trimethylsilyl group (for example, by treatment with potassium carbonate in methanol), followed by introduction of the second aryl group by a Sonogashira coupling (Sonogashira, K.; Yohda, Y. and Hagihara, N.; *Tetrahedron Lett.*, 1975, 4467), gave the diaryl species G which, upon deprotection with, for example, formic acid, gave the final product H.

This route is an attractive one for the parallel synthesis of a series of related compounds in which group $Ar_2$ is constant, but group $Ar_1$ represents a number of different aryl groups. Common intermediate F can be prepared in bulk, and simply treated with the appropriate aryliodide under Sonogashira conditions to yield the desired products.

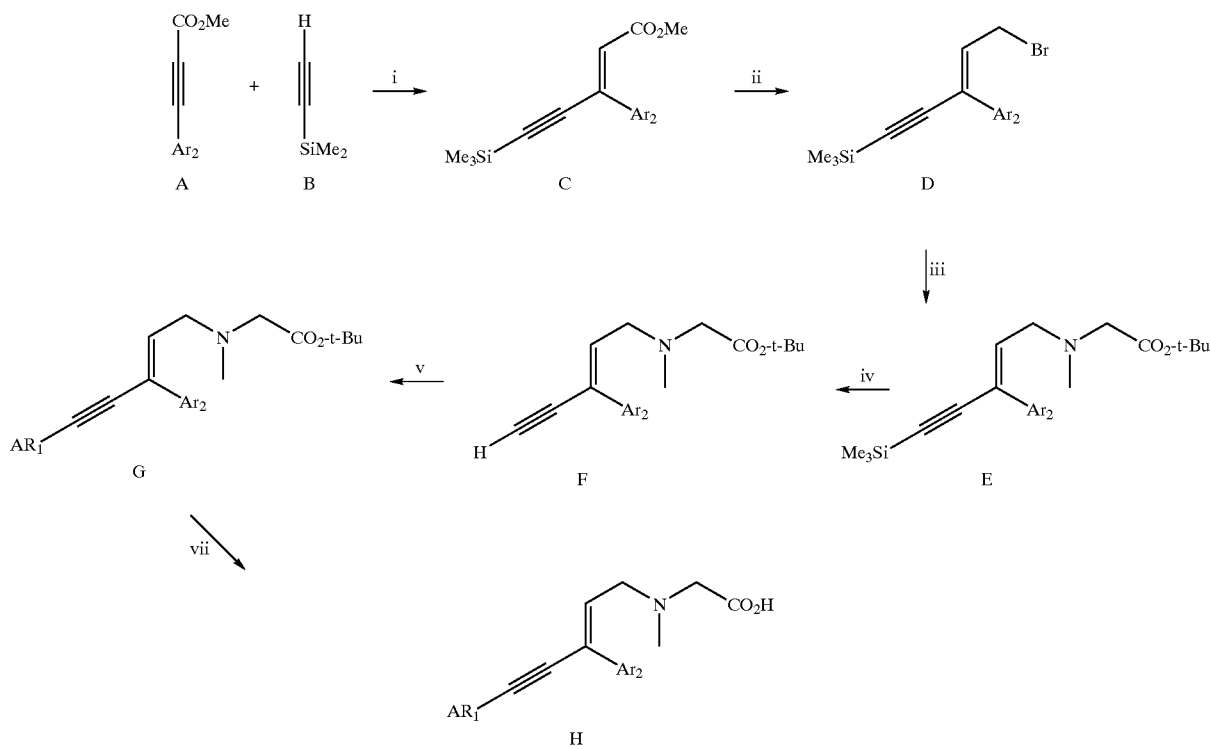

Scheme 1

Reagents: (i) Pd(OAc)$_2$, phosphine ligand; (ii) (a) DIBAL-H, (b) NBS, PPh$_3$; (iii) t-Bu sarcosine, K$_2$CO$_3$, KI; (iv) K$_2$CO$_3$, MeOH; (v) Ar$_1$-I, CuI, Pd(PPh$_3$)$_4$, Et$_3$N; (vi) formic acid, 50° C.

Alternatively, such compounds may also be prepared according to the route shown in Scheme 2, below. This route complements that shown above, in that it allows the parallel synthesis of a series of related compounds in which group $Ar_1$ is constant, but group $Ar_2$ represents a number of different aryl groups. In this case, common intermediate L can be prepared in bulk, and simply treated with the appropriate arylpropiolic ester O (readily accessible from aryliodide M by treatment with propiolic ester N in the presence of CuI and Pd(PPh$_3$)$_4$), under the conditions outlined above, to yield, after deprotection, products H.

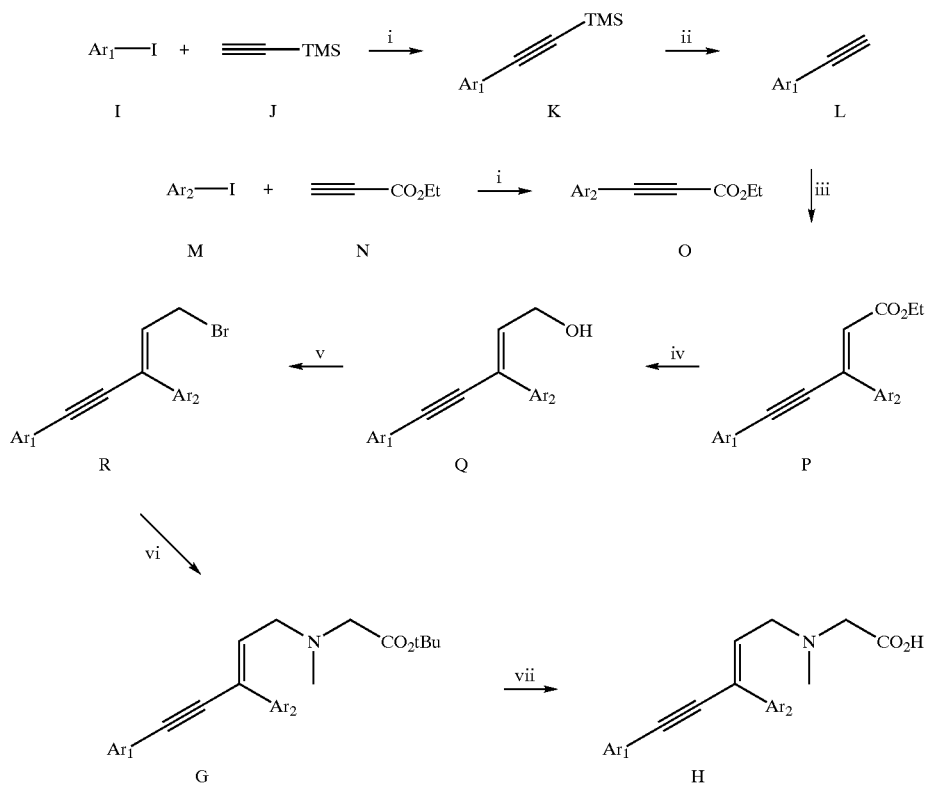

Reagents: (i) CuI, Pd(PPh$_3$)$_4$, Et$_3$N; (ii) K$_2$CO$_3$, MeOH; (iii) Pd(OAc)$_2$, phosphine ligand; PhMe; (iv) DIBAL-H, PhMe, -78° C.; (v) NBS, PPh$_3$; (vi) t-Bu sarcosine, K$_2$CO$_3$, KI, MeCN; (vii) formic acid, 50° C.

To prepare compounds in which Ar$_1$ is Aryl-substituted phenyl (Ar$_3$-phenyl), the following synthesis (Scheme 3) is useful. Intermediate F can be prepared according to Scheme 1, then coupled to bromoiodobenzene via Sonogashira coupling to yield species S. The aryliodide of species S can then be reacted with a boronic acid (Ar$_3$-boronic acid) under Suzuki coupling conditions to give intermediate G'. (G' is equivalent to G, Scheme 1, Where Ar$_1$ is Ar$_3$-phenyl). G' can then be deprotected as in Scheme 1 to give H'.

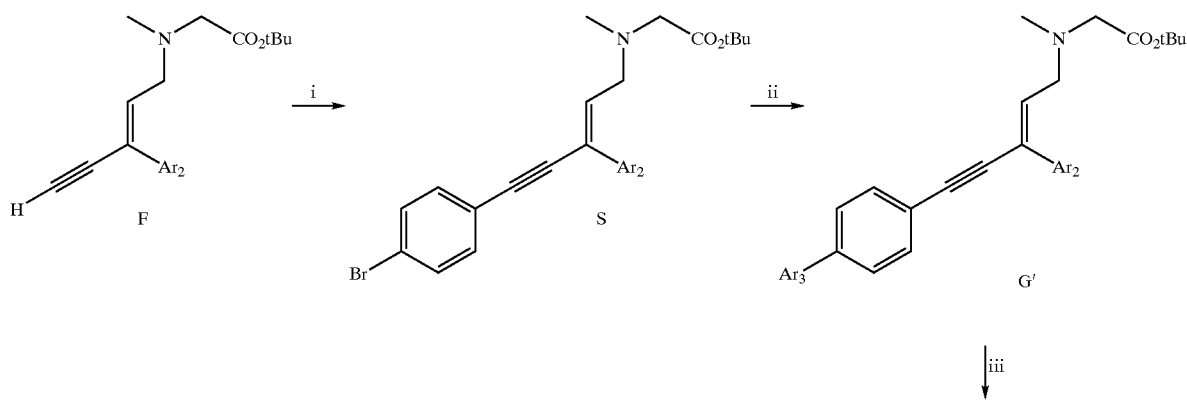

-continued

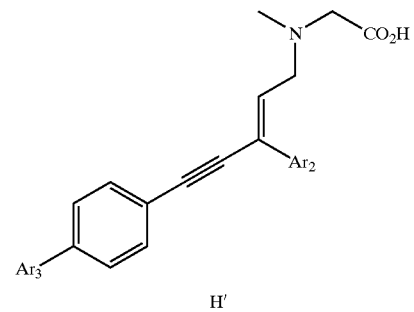

(i) 4-bromoiodobenzene, Pd(PPh$_3$)$_4$, CuI, Et$_3$N, r.t, overnight; (ii) Ar$_3$-boronic acid, Pd(PPh$_3$)$_4$, 2M Na$_2$CO$_3$, DME, 110° C., 1 hour, (iii) formic acid, 40° C., overnight.

Compounds which inhibit GlyT-1 mediated glycine transport will increase glycine concentrations at NMDA receptors, which receptors are located in the forebrain, among other locations. This concentration increase elevates the activity of NMDA receptors, thereby alleviating schizophrenia and enhancing cognitive function. Alternatively, compounds that interact directly with the glycine receptor component of the NMDA receptor can have the same or similar effects as increasing or decreasing the availability of extracellular glycine caused by inhibiting or enhancing GlyT-1 activity, respectively. See, for example, Pitkadnen et al., *Eur. J. Pharmacol.*, 253, 125–129 (1994); Thiels et al., *Neuroscience*, 46, 501–509 (1992); and Kretschmer and Schmidt, *J. Neurosci.*, 16, 1561–1569 (1996).

The compounds of the invention are, for instance, administered orally, sublingually, rectally, nasally, vaginally, topically (including the use of a patch or other transdermal delivery device), by pulmonary route by use of an aerosol, or parenterally, including, for example, intramuscularly, subcutaneously, intraperitoneally, intraarterially, intravenously or intrathecally. Administration can be by means of a pump for periodic or continuous delivery. The compounds of the invention are administered alone, or are combined with a pharmaceutically-acceptable carrier or excipient according to standard pharmaceutical practice. For the oral mode of administration, the compounds of the invention are used in the form of tablets, capsules, lozenges, chewing gum, troches, powders, syrups, elixirs, aqueous solutions and suspensions, and the like. In the case of tablets, carriers that are used include lactose, sodium citrate and salts of phosphoric acid. Various disintegrants such as starch, and lubricating agents such as magnesium stearate and talc, are commonly used in tablets. For oral administration in capsule form, useful diluents are lactose and high molecular weight polyethylene glycols. If desired, certain sweetening and/or flavoring agents are added. For parenteral administration, sterile solutions of the compounds of the invention are usually prepared, and the pHs of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzylchromium chloride, and the usual quantities of diluents and/or carriers. For pulmonary administration, diluents and/or carriers will be selected to be appropriate to allow the formation of an aerosol.

Suppository forms of the compounds of the invention are useful for vaginal, urethral and rectal administrations. Such suppositories will generally be constructed of a mixture of substances that is solid at room temperature but melts at body temperature. The substances commonly used to create such vehicles include theobroma oil, glycerinated gelatin, hydrogenated vegetable oils, mixtures of polyethylene glycols of various molecular weight and fatty acid esters of polyethylene glycol. See, Remington's Pharmaceutical Sciences, 16th Ed., Mack Publishing, Easton, Pa., 1980, pp. 1530–1533 for further discussion of suppository dosage forms. Analogous gels or creams can be used for vaginal, urethral and rectal administrations.

Numerous administration vehicles will be apparent to those of ordinary skill in the art, including without limitation slow release formulations, liposomal formulations and polymeric matrices.

Examples of pharmaceutically acceptable acid addition salts for use in the present invention include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic and arylsulphonic acids, for example. Examples of pharmaceutically acceptable base addition salts for use in the present invention include those derived from non-toxic metals such as sodium or potassium, ammonium salts and organoamino salts such as triethylamine salts. Numerous appropriate such salts will be known to those of ordinary skill.

The physician or other health care professional can select the appropriate dose and treatment regimen based on the subject's weight, age, and physical condition. Dosages will generally be selected to maintain a serum level of compounds of the invention between about 0.01 µg/cc and about 1000 µg/cc, preferably between about 0.1 µg/cc and about 100 µg/cc. For parenteral administration, an alternative measure of preferred amount is from about 0.001 mg/kg to about 10 mg/kg (alternatively, from about 0.01 mg/kg to about 10 mg/kg), more preferably from about 0.01 mg/kg to about 1 mg/kg (from about 0.1 mg/kg to about 1 mg/kg), will be administered. For oral administrations, an alternative measure of preferred administration amount is from about 0.001 mg/kg to about 10 mg/kg (from about 0.1 mg/kg to about 10 mg/kg), more preferably from about 0.01 mg/kg to about 1 mg/kg (from about 0.1 mg/kg to about 1 mg/kg). For administrations in suppository form, an alternative measure of preferred administration amount is from about 0.1 mg/kg to about 10 mg/kg, more preferably from about 0.1 mg/kg to about 1 mg/kg.

For use in assaying for activity in inhibiting glycine transport, eukaryokic cells, preferably QT-6 cells derived from quail fibroblasts, have been transfected to express one of the three known variants of human GlyT-1, namely GlyT-1a, GlyT-1b or GlyT-1c, or human GlyT-2. The sequences of these GlyT-1 transporters are described in Kim et al., *Molec. Pharm.* 45: 608–617, 1994, excepting that the sequence encoding the extreme N-terminal of GlyT-1a was merely inferred from the corresponding rat-derived sequence. This N-terminal protein-encoding sequence has now been confirmed to correspond to that inferred by Kim et al. The sequence of the human GlyT-2 is described by Albert et al., U.S. application Ser. No. 08/700,013, filed Aug. 20, 1996, which is incorporated herein by reference in its entirety. Suitable expression vectors include pRc/CMV (Invitrogen), Zap Express Vector (Stratagene Cloning Systems, LaJolla, Calif.; hereinafter "Stratagene"), pBk/CMV or pBk-RSV vectors (Stratagene), Bluescript II SK+/− Phagemid Vectors (Stratagene), LacSwitch (Stratagene), pMAM and pMAM neo (Clontech), among others. A suitable expression vector is capable of fostering expression of the included GlyT DNA in a suitable host cell, preferably a non-mammalian host cell, which can be eukaryotic, fungal, or prokaryotic. Such preferred host cells include amphibian, avian, fungal, insect, and reptilian cells.

EXAMPLES

Example 1

1-Methoxycarbonyl-2-phenyl-4-trimethylsilyl-1-buten-4-yne (C)

To a solution of palladium acetate (28 mg, 0.125 mmol) in anhydrous toluene (5 mL) was added tris(2,6-dimethoxyphenyl)phosphine (55 mg, 0.125 mmol). After 15 minutes a solution of methyl phenylpropiolate (1.00 g, 6.24 mmol) in anhydrous toluene (5 mL) was added. After an additional 5 minutes trimethylsilylacetylene (0.88 mL, 0.61 g, 6.24 mmol) was added. After 16 hours the reaction mixture was concentrated. Column chromatography (10% ethyl acetate/hexanes) provided enyne C (1.39 g, 86%) as a yellow oil. C: $^1$H NMR (CDCl3, 300 MHz) 0.21 (s, 9H), 3.62 (s, 3H), 6.34 (s, 1H), 7.33–7.44 (m, 5H).

Example 2

1-Hydroxy-3-phenyl-5-trimethylsilyl-2-penten-4-yne

A solution of the ester C (1.30 g, 5.03 mmol) in anhydrous toluene (20 mL) was chilled in a dry ice/acetone bath. A 1.0 M solution of diisobutylaluminum hydride in toluene (12.6 mL, 12.6 mmol) was added. After 5 minutes the chilling bath was removed. After a further 15 minutes the reaction mixture was re-chilled in an ice bath. The reaction was quenched with the addition of celite and sodium sulphate decahydrate. The slurry was diluted with ethyl acetate and filtered through celite. The filter cake was washed 3 times with ethyl acetate. The filtrate was washed with water and brine, dried (sodium sulphate), filtered, and concentrated to provide the intermediate alcohol (0.821 g, 71%) as a yellow oil.: $^1$H NMR (CDCl3, 300 MHz) 0.20 (s, 9H), 1.40 (t, 1H), 4.31 (dd, 2H), 6.37 (t, 1H), 7.33–7.37 (m, 5H).

Example 3

1-Bromo-3-phenyl-5-trimethylsilyl-2-penten-4-yne (D)

A solution of the above alcohol (0.82 g, 3.56 mmol) in anhydrous dichloromethane (20 mL) was chilled in a dry ice/acetonitrile bath. Triphenylphosphine (1.40 g, 5.34 mmol) and N-bromosuccinimide (0.95 g, 5.34 mmol) were added. After 30 minutes the reaction was quenched with saturated sodium bicarbonate. The reaction mixture was partitioned between saturated sodium bicarbonate and dichloromethane. The organic phase was washed with brine, dried (sodium sulphate), filtered, and concentrated to provide crude allylic bromide D, used directly in the next step.

Example 4

N-(3-Phenyl-5-(trimethylsilyl)-2-penten-4-yn-1-yl)-sarcosine, $^t$butyl ester (E)

To a solution of the above bromide in anhydrous acetonitrile (15 mL) was added t-butyl sarcosine hydrochloride (0.71 g, 3.90 mmol), potassium carbonate (4.91 g, 35.5 mmol), and potassium iodide (2.95 g, 17.8 mmol). After 16 hours the reaction mixture was filtered through celite. The filter cake was washed with ethyl acetate. The filtrate was poured into water and extracted with ethyl acetate. The organic phase was washed with water and brine, dried (sodium sulphate), filtered, and concentrated. Column chromatography (25% ethyl acetate/hexanes) provided product E (0.74 g, 58% over 2 steps) as a pale yellow oil. E: $^1$H NMR (CDCl$_3$, 300 MHz) 0.19 (s, 9H), 1.41 (s, 9H), 2.32 (s, 3H), 3.10 (s, 2H), 3.31 (d, 2H), 6.33 (t, 1H), 7.26–7.38 (m, 5H).

Example 5

N-(3-Phenyl-2-penten-4-yn-1-yl)-sarcosine, $^t$butyl ester (F)

To a solution of the above compound (0.74 g, 2.06 mmol) in methanol (10 mL) was added potassium carbonate (1.42 g, 10.3 mmol). After 20 minutes the reaction mixture was poured into water and extracted 2 times with ethyl acetate. The combined organic extracts were washed with brine, dried (sodium sulphate), filtered, and concentrated to provide terminal acetylene F (0.58 g, 99%) as an off-white solid. F: $^1$H NMR (CDCl$_3$, 300 MHz) 1.41 (s, 9H), 2.33 (s, 3H), 2.96 (s, 1H), 3.10 (s, 2H), 3.33 (d, 2H), 6.37 (t, 1H), 7.26–7.39 (m, 5H).

Example 6-1

N-(5-(4-Fluorophenyl)-3-phenyl-2-penten-4-yn-1-yl)-sarcosine, $^t$butyl ester, (G)

To a solution of the terminal acetylene F (50 mg, 0.175 mmol) in triethylamine (2 mL) was added 4-fluoroiodobenzene (26 µL, 51 mg, 0.228 mmol), tetrakis(triphenylphosphine)palladium(O) (20 mg, 0.0175 mmol), and copper(I) iodide (10 mg, 0.0525 mmol). After 16 hours the reaction mixture was diluted with dichloromethane and filtered. The filtrate was concentrated. Column chromatography (25% ethyl acetate/hexanes) provided acetylene G (51 mg, 77%) as a yellow oil. G: $^1$H NMR (CDCl$_3$, 300 MHz) 1.42 (s, 9H), 2.35 (s, 3H), 3.13 (s, 2H), 3.36 (d, 2H), 6.37 (t, 1H), 7.00 (dd, 2H), 7.26–7.44 (m, 7H).

In a similar fashion the following compounds were prepared from intermediate F and 1.3 equivalents of the corresponding aryliodide treated under the conditions described above.:

6-2: N-(5-(2-Fluorophenyl)-3-phenyl-2-penten-4-yn-1-yl)-sarcosine, $^t$butyl ester, (G)

Prepared in a similar fashion from 2-fluoroiodobenzene to provide 45 mg (68%) of a yellow oil. $^1$H NMR (CDCl$_3$, 300 MHz) 1.42 (s, 9H), 2.36 (s, 3H), 3.14 (s, 2H), 3.39 (d, 2H), 6.43 (t, 1H), 7.06 (dd, 2H), 7.24–7.44 (m, 7H).

6-3: N-(5-(2,4-Difluorophenyl)-3-phenyl-2-penten-4-yn-1-yl)-sarcosine, ᵗbutyl ester, (G)

Prepared in a similar fashion from 2,4-difluoroiodobenzene to provide 49 mg (70%) of a yellow oil. ¹HNMR (CDCl₃, 300 MHz) 1.42 (s, 9H), 2.36 (s, 3H), 3.13 (s, 2H), 3.38 (d, 2H), 6.42 (t, 1H), 6.83 (dd, 2H), 7.26–7.44 (m, 6H).

6-4: N-(5-(3-Nitrophenyl)-3-phenyl-2-penten-4-yn-1-yl)-sarcosine, ᵗbutyl ester, (G)

Prepared in a similar fashion from 3-nitroiodobenzene to provide 73 mg (102%) of a yellow oil. ¹H NMR (CDCl₃, 300 MHz) 1.42 (s, 9H), 2.36 (s, 3H), 3.13 (s, 2H), 3.38 (d, 2H), 6.45 (t, 1H), 7.26–7.40 (m, 5H), 7.48 (dd, 1H), 7.72 (d, 1H), 8.13 (d, 1H), 8.27 (s, 1H).

6-5: N-(5-(4-Nitrophenyl)-3-phenyl-2-penten-4-yn-1-yl)-sarcosine, ᵗbutyl ester, (G)

Prepared in a similar fashion from 4-nitroiodobenzene to provide 31 mg (44%) of a yellow oil. ¹H NMR (CDCl₃, 300 MHz) 1.42 (s, 9H), 2.36 (s, 3H), 3.14 (s, 2H), 3.38 (d, 2H), 6.47 (t, 1H), 7.34–7.43 (m, 5H), 7.57 (d, 2H), 8.17 (d, 2H).

6-6: N-(3-Phenyl-5-(2-thiomethylphenyl)-2-penten-4-yn-1-yl)-sarcosine, ᵗbutyl ester, (G)

Prepared in a similar fashion from 2-thiomethyliodobenzene to provide 19 mg (26%) of a yellow oil. ¹H NMR (CDCl₃) 1.42 (s, 9H), 2.36 (s, 3H), 2.46 (s, 3H), 3.14 (s, 2H), 3.39 (d, 2H), 6.45 (t, 1H), 7.06 (dd, 1H), 7.14 (d, 1H), 7.24–7.40 (m, 6H), 7.46 (d, 1H).

6-7: N-(5-(4-Chlorophenyl)-3-phenyl-2-penten-4-yn-1-yl)-sarcosine, ᵗbutyl ester, (G)

Prepared in a similar fashion from 4-chloroiodobenzene to provide 52 mg (75%) of a yellow oil. ¹H NMR (CDCl₃, 300 MHz) 1.42 (s, 9H), 2.35 (s, 3H), 3.13 (s, 2H), 3.36 (d, 2H), 6.38 (t, 1H), 7.26–7.39 (m, 9H).

6-8: N-(5-(4-Isopropylphenyl)-3-phenyl-2-penten-4-yn-1-yl)-sarcosine, ᵗbutyl ester, (G)

Prepared in a similar fashion from 4-isopropyliodobenzene to provide 38 mg (53%) of a yellow oil. ¹H NMR (CDCl₃, 300 MHz) 1.23 (d, 6H), 1.42 (s, 9H), 2.36 (s, 3H), 2.89 (hept, 1H), 3.13 (s, 2H), 3.36 (d, 2H), 6.36 (t, 1H), 7.16 (d, 2H), 7.26–7.42 (m, 7H).

6-9: N-(5-(3,5-Bis(trifluoromethyl)phenyl)-3-phenyl-2-penten-4-yn-1-yl)-sarcosine, ᵗbutyl ester, (G)

Prepared in a similar fashion from 3,5-Bis(trifluoromethyl)iodobenzene to provide 40 mg (46%) of a yellow oil. ¹H NMR (CDCl₃, 300 MHz) 1.42 (s, 9H), 2.36 (s, 3H), 3.14 (s, 2H), 3.38 (d, 2H), 6.47 (t, 1H), 7.26–7.44 (m, 5H), 7.77 (s, 1H), 7.86 (s, 2H).

6-10: N-(3,5-Diphenyl-2-penten-4-yn-1-yl)-sarcosine, ᵗbutyl ester, (G)

Prepared in a similar fashion from iodobenzene to provide 46 mg (33%) of a yellow oil. ¹H NMR (CDCl₃, 300 MHz) 1.42 (s, 9H), 2.36 (s, 3H), 3.13 (s, 2H), 3.36 (d, 2H), 6.38 (t, 1H), 7.26–7.46 (m, 10H).

6-11: N-(3-Phenyl-5-(4-thiomethylphenyl)-2-penten-4-yn-1-yl)-sarcosine, ᵗbutyl ester, (G)

Prepared in a similar fashion from 4-thiomethyliodobenzene to provide 30.0 mg (70%) of a yellow oil.

6-12: N-(3-Phenyl-5-(4-methylphenyl)-2-penten-4-yn-1-yl)-sarcosine, ᵗbutyl ester, (G)

Prepared in a similar fashion from 4-methyliodobenzene to provide 33.0 mg (85%) of a yellow oil.

6-13: N-(5-(3-Thiophene)-3-phenyl-2-penten-4-yn-1-yl)-sarcosine, ᵗbutyl ester, (G)

Prepared in a similar fashion from 3-iodothiophene to provide 30.0 mg (78%) of a brown oil.

6-14: N-(3-Phenyl-5-(4-tbutylphenyl)-2-penten-4-yn-1-yl)-sarcosine, ᵗbutyl ester, (G)

Prepared in a similar fashion from 4-t-butyliodobenzene to provide 38.0 mg (86%) of a yellow oil.

6-15: N-(5-(4-Methoxyphenyl)-3-phenyl-2-penten-4-yn-1-yl)-sarcosine, ᵗbutyl ester, (G)

Prepared in a similar fashion from 4-methoxyiodobenzene to provide 31.0 mg (73%) of a yellow oil.

6-16: N-(5-(2-Isopropylphenyl)-3-phenyl-2-penten-4-yn-1-yl)-sarcosine, ᵗbutyl ester, (G)

Prepared in a similar fashion from 2-isopropyliodobenzene to provide 27.0 mg (64%) of an amber oil.

6-17: N-(5-(4-diphenyl)-3-phenyl-2-penten-4-yn-1-yl)-sarcosine, ᵗbutyl ester, (G)

Prepared in a similar fashion from 4-biphenyliodobenzene to provide 260 mg (85%) of a yellow oil.

6-18: N-(5-(4-trifluoromethylphenyl)-3-phenyl-2-penten-4-yn-1-yl)-sarcosine, ᵗbutyl ester, (G)

Prepared in a similar fashion from 4-trifluoromethyliodobenzene to provide 240 mg 80%) of a yellow oil.

6-19: N-(5-(4-benzylphenyl)-3-phenyl-2-penten-4-yn-1-yl)-sarcosine, ᵗbutyl ester, (G)

Prepared in a similar fashion from 4-benzyliodobenzene to provide 240 mg (80%) of a light yellow oil.

6-20: N-(5-(4-ethylphenyl)-3-phenyl-2-penten-4-yn-1-yl)-sarcosine, ᵗbutyl ester, (G)

Prepared in a similar fashion from 4-ethyliodobenzene to provide 240 mg (88%) of product. 6-20: ¹H NMR (CDCl₃, 300 MHz) 1.22 (t, 3H), 1.43 (s, 9H), 2.36 (s, 3H), 2.63(q, 2H), 3.13 (s, 2H), 3.36 (d, 2H), 6.37 (t, 1H), 7.13 (d, 2H), 7.26–7.43 (m, 7H).

6-21: N-(5-(4-npropylphenyl)-3-phenyl-2-penten-4-yn-1-yl)-sarcosine, ᵗbutyl ester, (G)

Prepared in a similar fashion from 4-n-propyliodobenzene to provide 240 mg (85%) of product. 6-21: ¹H NMR (CDCl₃, 300 MHz) 0.93 (t, 3H),1.43 (s, 9H), 1.57 (sextet, 2H), 2.36 (s, 3H), 2.57 (t, 2H), 3.14 (s, 2H), 3.37 (d, 2H), 6.37 (t, 1H), 7.12 (d, 2H), 7.25–7.43 (m, 7H).

6-22: N-(5-(4-nbutylphenyl)-3-phenyl-2-penten-4-yn-1-yl)-sarcosine, ᵗbutyl ester, (G)

Prepared in a similar fashion from 4-n-butyliodobenzene to provide 260 mg (89%) of a yellow oil.

6-23: N-(5-(4-npentylphenyl)-3-phenyl-2-penten-4-yn-1-yl)-sarcosine, ᵗbutyl ester, (G)

Prepared in a similar fashion from 4-n-pentyliodobenzene to provide 240 mg (79%) of a yellow oil.

6-24: N-(5-(4-phenoxyphenyl)-3-phenyl-2-penten-4-yn-1-yl)-sarcosine, ᵗbutyl ester, (G)

Prepared in a similar fashion from 4-phenoxyiodobenzene to provide 34.7 mg (56%) of a yellow film.

6-25: N-(5-(1-naphthyl)-3-phenyl-2-penten-4-yn-1-yl)-sarcosine, ᵗbutyl ester, (G)

Prepared in a similar fashion from 1-iodonaphthalene to provide 35.8 mg (63.5%) of product. 6-25: $^1$H NMR (CDCl$_3$, 300 MHz) 1.43 (s, 9H), 2.40 (s, 3H), 3.17 (s, 2H), 3.42 d, 2H), 6.53 (t, 1H), 7.33–7.57 (m, 8H), 7.67 (d, 1H), 7.75–7.85 (m, 2H), 8.30 (d, 1H).

6-26: N-(5-(4-methylphenyl)-3-phenyl-2-penten-4-yn-1-yl)-sarcosine, ᵗbutyl ester, (G)

Prepared in a similar fashion from 4-methyliodobenzene to provide 34.7 mg (88%) of a light yellow oil.

6-27: N-(5-(3-isopropylphenyl)-3-phenyl-2-penten-4-yn-1-yl)-sarcosine, ᵗbutyl ester, (G)

Prepared in a similar fashion from 3-isopropyliodobenzene to provide 17.6 mg (42%) of product. 6-27: $^1$H NMR (CDCl$_3$, 300 MHz) 1.23 (d, 6H),1.42 (s, 9H), 2.36 (s, 3H), 2.87 (septtet, 1H), 3.13 (s, 2H), 3.36 (d, 2H), 6.38 (t, 1H), 7.15–7.42 (m, 8H), 7.70–7.71 (m, 1H).

6-28: N-(5-(2-naphthyl)-3-phenyl-2-penten-4-yn-1-yl)-sarcosine, ᵗbutyl ester, (G)

Prepared in a similar fashion from 2-iodonaphthalene to provide 30.0 mg (69%) of a colourless oil.

6-29: N-(5-(3,4-dimethylphenyl)-3-phenyl-2-penten-4-yn-1-yl)-sarcosine, ᵗbutyl ester, (G)

Prepared in a similar fashion from 3,4-dimethyliodobenzene to provide 40.0 mg (98%) of a yellow film.

6-30: N-(5-(2-isopropylphenyl)-3-phenyl-2-penten-4-yn-1-yl)-sarcosine, ᵗbutyl ester, (G)

Prepared in a similar fashion from 2-isopropyliodobenzene to provide 27.0 mg (64%) of an amber oil.

6-31: N-(5-(3,4-methylenedioxyphenyl)-3-phenyl-2-penten-4-yn-1-yl)-sarcosine, ᵗbutyl ester, (G)

Prepared in a similar fashion from 3,4-methylenedioxyiodobenzene to provide 40.0 mg (94%) of a yellow oil.

6-32: N-(5-(4-pyrrolylphenyl)-3-phenyl-2-penten-4-yn-1-yl)-sarcosine, ᵗbutyl ester, (G)

Prepared in a similar fashion from 4-pyrrolyliodobenzene to provide 41.0 mg (92%) of a light yellow oil.

6-33: N-(5-(4-trifluoromethoxyphenyl)-3-phenyl-2-penten-4-yn-1-yl)-sarcosine, ᵗbutyl ester, (G)

Prepared in a similar fashion from 4-trifluoromethoxyiodobenzene to provide 28.5 mg (61%) of product. 6-33: $^1$H NMR (CDCl3, 300 MHz) 1.42 (s, 9H), 2.35 (s, 3H), 3.13 (s, 2H), 3.36 (d, 2H), 6.39 (t, 1H), 7.15 (d, 2H), 7.26–7.39 (d, 2H), 7.46 (d, 2H).

6-34: N-(5-(3,4-dimethoxyphenyl)-3-phenyl-2-penten-4-yn-1-yl)-sarcosine, ᵗbutyl ester, (G)

Prepared in a similar fashion from 3,4-dimethoxyiodoenzene to provide 35.0 mg (80%) of a colourless oil.

In a similar fashion the following compounds are prepared from intermediate F and 1.3 equivalents of the corresponding aryliodide treated under the conditions described above:

6-35: N-(5-(2-quinoline)-3-phenyl-2-penten-4-yn-1-yl)-sarcosine, ᵗbutyl ester, (G)

Prepare in a similar fashion from 2-iodoquinolene.

6-36: N-(5-(indanyl)-3-phenyl-2-penten-4-yn-1-yl)-sarcosine, ᵗbutyl ester, (G)

Prepare in a similar fashion from iodoindane.

Example 7-1

N-(5-(4-Fluorophenyl)-3-phenyl-2-penten-4-yn-1-yl)-sarcosine, (H)

A solution of t-butyl ester 6-1 (51 mg, 0.135 mmol) in 96% formic acid was heated at 40 C. for 16 hours. The reaction mixture was cooled and concentrated. The residue was taken up into dichloromethane and passed through a 2 g solid phase extraction tube, eluting with dichloromethane, then ethyl acetate, then methanol. The methanol fraction was concentrated to provide amino acid 7-1 (39 mg, 90%) as a colourless foam: $^1$H NMR (CDCl$_3$, 300 MHz) 2.72 (s, 3H), 3.49 (s, 2H), 3.92 (d, 2H), 6.38 (t, 1H), 6.98 (dd, 2H), 7.26–7.42 (m, 7H). HRMS calc 324.1400, found 324.1386.

In a similar fashion the following compounds were prepared from the corresponding intermediate treated under the conditions described above:

7-2: N-(5-(2-Fluorophenyl)-3-phenyl-2-penten-4-yn-1-yl)-sarcosine, (H)

Prepared in a similar fashion from intermediate 6-2 to provide 31 mg (81%) of a colourless foam. $^1$H NMR (CDCl$_3$, 300 MHz) 2.68 (s, 3H), 3.47 (s, 2H), 3.90 (s, 2H), 6.43 (s, 1H), 7.05 (dd, 2H), 7.23–7.42 (m, 7H). HRMS calc 324.1400, found 324.1408.

7-3: N-(5-(2,4-Difluorophenyl)-3-phenyl-2-penten-4-yn-1-yl)-sarcosine, (H)

Prepared in a similar fashion from intermediate 6-3 to provide 34 mg (82%) of a colourless foam. $^1$H NMR (CDCl$_3$, 300 MHz) 2.70 (s, 3H), 3.48 (s, 2H), 3.91 (s, 2H), 6.42 (s, 1H), 6.78 (dd, 2H), 7.26–7.38 (m, 6H). HRMS calc 342.1306, found 342.1333.

7-4: N-(5-(3-Nitrophenyl)-3-phenyl-2-penten-4-yn-1-yl)-sarcosine, (H)

Prepared in a similar fashion from intermediate 6-4 to provide 42 mg (68%) of a colourless foam. $^1$H NMR (CDCl$_3$, 300 MHz) 2.72 (s, 3H), 3.50 (s, 2H), 3.94 (d, 2H), 6.50 (t, 1H), 7.26–7.48 (m, 6H), 7.70 (d, 1H), 8.12 (d, 1H), 8.22 (s, 1H). HRMS calc 351.1345, found 351.1353.

7-5: N-(5-(4-Nitrophenyl)-3-phenyl-2-penten-4-yn-1-yl)-sarcosine, (H)

Prepared in a similar fashion from intermediate 6-5 to provide 21 mg (80%) of a colourless foam. $^1$H NMR (CDCl3, 300 MHz) 2.66 (s, 3H), 3.43 (s, 2H), 3.85 (d, 2H), 6.51 (s, 1H), 7.26–7.53 (m, 5H), 7.54 (d, 2H), 8.14 (d, 2H).

7-6: N-(3-Phenyl-5-(2-thiomethylphenyl)-2-penten-4-yn-1-yl)-sarcosine, (H)

Prepared in a similar fashion from intermediate 6-6 to provide 14 mg (87%) of a colourless foam. $^1$H NMR (CDCl$_3$, 300 MHz) 2.42 (s, 3H), 2.66 (s, 3H), 3.48 (s, 2H), 3.88 (s, 2H), 6.40 (s, 1H), 7.12–7.68 (m, 9H).

7-7: N-(5-(4-Chlorophenyl)-3-phenyl-2-penten-4-yn-1-yl)-sarcosine, (H)

Prepared in a similar fashion from intermediate 6-7 to provide 40 mg (90%) of a colourless foam. $^1$H NMR (CDCl$_3$, 300 MHz) 2.68 (s, 3H), 3.48 (s, 2H), 3.87 (s, 2H), 6.39 (s, 1H), 7.24–7.37 (m, 9H). HRMS calc 340.1104, found 340.1097.

7-8: N-(5-(4-Isopropylphenyl)-3-phenyl-2-penten-4-yn-1-yl)-sarcosine, (H)

Prepared in a similar fashion from intermediate 6-8 to provide 32 mg (99%) of a colourless foam. $^1$H NMR (CDCl$_3$, 300 MHz) 1.21 (d, 6H), 2.65 (s, 3H), 2.86 (hept, 1H), 3.43 (s, 2H), 3.86 (d, 2H), 6.36 (t, 1H), 7.14 (d, 2H), 7.26–7.36 (m, 7H). HRMS calc 348.1964, found 348.1998.

7-9: N-(5-(3,5-Bis(trifluoromethyl)phenyl)-3-phenyl-2-penten-4-yn-1-yl)-sarcosine, (H)

Prepared in a similar fashion from intermediate 6-9 to provide 26 mg (76%) of a colourless foam. $^1$H NMR (CDCl$_3$, 300 MHz) 2.67 (s, 3H), 3.46 (s, 2H), 3.87 (d, 2H), 6.52 (t, 1H), 7.26–7.40 (m, 5H), 7.77 (s, 1H), 7.83 (s, 2H). HRMS calc 442.1242, found 442.1173.

7-10: N-(3,5-Diphenyl-2-penten-4-yn-1-yl)-sarcosine, (H)

Prepared in a similar fashion from intermediate 6-10 to provide 18 mg (46%) of a colourless foam. $^1$H NMR (CDCl$_3$, 300 MHz) 2.69 (s, 3H), 3.48 (s, 2H), 3.89 (d, 2H), 6.40 (t, 1H), 7.26–7.44 (m, 10H). HRMS calc 306.1494, found 306.1432.

7-11: N-(5-(4-diphenyl)-3-phenyl-2-penten-4-yn-1-yl)-sarcosine, (H)

Prepared in a similar fashion from intermediate 6-17 to provide 220.0 mg (97%) of a yellow solid.

7-12: N-(5-(4-trifluoromethylphenyl)-3-phenyl-2-penten-4-yn-1-yl)-sarcosine, (H)

Prepared in a similar fashion from intermediate 6-18 to provide 200.0 mg (96%) of a yellow film.

7-13: N-(5-(4-benzylphenyl)-3-phenyl-2-penten-4-yn-1-yl)-sarcosine, (H)

Prepared in a similar fashion from intermediate 6-19 to provide 190.0 mg (87%) of a light yellow solid.

7-14: N-(5-(4-ethylphenyl)-3-phenyl-2-penten-4-yn-1-yl)-sarcosine, (H)

Prepared in a similar fashion from intermediate 6-20, to provide 176.1 mg (86%) of a green-grey solid.

7-15: N-(5-(4-$^n$propylphenyl)-3-phenyl-2-penten-4-yn-1-yl)-sarcosine, (H)

Prepared in a similar fashion from intermediate 6-21 to provide 190.9 mg (93%) of an orange-white solid.

7-16: N-(5-(4-$^n$butylphenyl)-3-phenyl-2-penten-4-yn-1-yl)-sarcosine, (H)

Prepared in a similar fashion from intermediate 6-22 to provide 206.0 mg (91%) of a yellow solid.

7-17: N-(5-(4-$^n$pentylphenyl)-3-phenyl-2-penten-4-yn-1-yl)-sarcosine, (H)

Prepared in a similar fashion from intermediate 6-23 to provide 204.4 mg (98%) of a yellow solid.

7-18: N-(5-(4-phenoxyphenyl)-3-phenyl-2-penten-4-yn-1-yl)-sarcosine, (H)

Prepared in a similar fashion from intermediate 6-24 to provide 33.0 mg (100%) of a light yellow solid.

7-19: N-(5-(1-naphthyl)-3-phenyl-2-penten-4-yn-1-yl)-sarcosine, (H)

Prepared in a similar fashion from intermediate 6-25 to provide 25.4 mg (82%) of a yellow oil.

7-20: N-(5-(4-methylphenyl)-3-phenyl-2-penten-4-yn-1-yl)-sarcosine, (H)

Prepared in a similar fashion from intermediate 6-26 to provide 12.6 mg (55%) of a yellow solid.

7-21: N-(5-(3-isopropylphenyl)-3-phenyl-2-penten-4-yn-1-yl)-sarcosine, (H)

Prepared in a similar fashion from intermediate 6-27 to provide 12.6 mg (83%) of a green-brown oil.

7-22: N-(5-(2-naphthyl)-3-phenyl-2-penten-4-yn-1-yl)-sarcosine, (H)

Prepared in a similar fashion from intermediate 6-28 to provide 25.1 mg (97%) of a yellow solid.

7-23: N-(5-(3,4-dimethylphenyl)-3-phenyl-2-penten-4-yn-1-yl)-sarcosine, (H)

Prepared in a similar fashion from intermediate 6-29 to provide 33.2 mg (97%) of a light yellow solid.

7-24: N-(5-(2-isopropylphenyl)-3-phenyl-2-penten-4-yn-1-yl)-sarcosine, (H)

Prepared in a similar fashion from intermediate 6-30 to provide 15.2 mg (66%) of a flaky yellow solid.

7-25: N-(5-(3,4-methylenedioxyphenyl)-3-phenyl-2-penten-4-yn-1-yl)-sarcosine, (H)

Prepared in a similar fashion from intermediate 6-31 to provide 9.5 mg (31%) of an off-white solid.

7-26: N-(5-(4-pyrrolylphenyl)-3-phenyl-2-penten-4-yn-1-yl)-sarcosine, (H)

Prepared in a similar fashion from intermediate 6-32 to provide 24.1 mg (68%) of a yellow solid.

7-27: N-(5-(4-trifluoromethoxyphenyl)-3-phenyl-2-penten-4-yn-1-yl)-sarcosine, (H)

Prepared in a similar fashion from intermediate 6-33 to provide 23.0 mg (92%) of a yellow solid.

7-28: N-(5-(3,4-dimethoxyphenyl)-3-phenyl-2-penten-4-yn-1-yl)-sarcosine, (H)

Prepared in a similar fashion from intermediate 6-34 to provide 25.7 mg (86%) of a yellow solid.

In a similar fashion the following compounds are prepared from the corresponding intermediate treated under the conditions described above:

7-29: N-(5-(2-quinoline)-3-phenyl-2-penten-4-yn-1-yl)-sarcosine

Prepare in a similar fashion from 6-35.

7-30: N-(5-(indanyl)-3-phenyl-2-penten-4-yn-1-yl)-sarcosine

Prepare in a similar fashion from 6-36.

Example 8-1

N-(3-Phenyl-5-(4-thiomethylphenyl)-2-penten-4-yn-1-yl)-sarcosine, (H)

A solution of $^t$butyl ester 6-11 G(vi) (30.0 mg, 0.0736 mmol) in 96% formic acid was heated at 50 C. for 3 hours. The reaction mixture was cooled and concentrated. The residue was taken up in dichloromethane and passed through a 2 g solid phase extraction tube, eluting with dichloromethane, then ethyl acetate, then methanol. The methanol fraction was concentrated to provide amino acid 8-1 (14.9 mg, 58%) as a light yellow solid.

In a similar fashion the following compounds were prepared from the corresponding intermediate under the conditions described above:

8-2: N-(5-(4-Methylphenyl)-3-phenyl-2-penten-4-yn-1-yl)-sarcosine, (H)

Prepared in a similar fashion from intermediate 6-12 to provide 30.0 mg (91%) of a light yellow solid.

8-3: N-(3-Phenyl-5-(3-thiophene)-2-penten-4-yn-1-yl)-sarcosine, (H)

Prepared in a similar fashion from intermediate 6-13 to provide 22.0 mg (87%) of a brown solid foam.

8-4: N-(3-Phenyl-5-(4-tbutylphenyl)-2-penten-4-yn-1-yl)-sarcosine, (H)

Prepared in a similar fashion from intermediate 6-14 to provide 22.9 mg (66%) of a light yellow solid.

Example 9

N-(5-(4-Bromophenyl)-3-phenyl-2-penten-4yn-1-yl) sarcosine $^t$butyl ester, (S)

To a solution of terminal acetylene F (3.25 g, 11.4 mmol) in Et3N (75 mL) was added 4-bromoiodobenzene (4.19 g, 14.8 mmol), Pd(PPh$_3$)$_4$ (1.32 g, 1.14 mmol), and CuI (0.65 g, 3.42 mmol). The mixture was stirred overnight, and concentrated. Column chromatography (10% EtOAc/hexanes) provided bromide S (3.84 g, 76%) as a yellow oil.

Example 10-1

N-(5-(4-(3furyl)phenyl)-3-phenyl-2-penten-4-yn-1-yl)-sarcosine $^t$Butyl ester, (G')

To a solution of bromide S (3.84 g, 8.72 mmol) in DME (25 mL) was added 3furanboronic acid (1.47 g, 13.1 mmol), Pd(PPh$_3$)$_4$ (1.01 g, 0.872 mmol), and 2M Na$_2$CO$_3$ (25 mL). The mixture was refluxed for 1 hour, cooled, and partitioned between EtOAc and water. The organic phase was washed with brine, dried (MgSO$_4$), filtered, and concentrated. Column chromatography (10–12.5% EtOAc/hexanes) provided ester G' (2.62 g, 78%) as a yellow oil.

In a similar fashion the following compounds were made from the corresponding boronic acid under the conditions described above:

10-2: N-(5-(4-(3-thiophene)phenyl)-3-phenyl-2-penten-4-yn-1-yl)-sarcosine $^t$Butyl ester, (G')

Prepared in a similar fashion from 3-thiopheneboronic acid to provide 21.0 mg (46%) of a colourless film.

In a similar fashion the following compounds are made from the corresponding boronic acid under the conditions described above:

10-3: N-(5-(4-(4Methyl-3-thiophene)phenyl)-3-phenyl-2-penten-4yn-1-yl)-sarcosine t-Butyl ester Prepare in a similar fashion from S and 4-methyl-3-thiopheneboronic acid.

10-4: N-(5-(4-(4Methyl-3-furyl)phenyl)-3-phenyl-2-penten-4yn-1-yl)-sarcosine t-Butyl ester Prepare in a similar fashion from S and 4-methyl-3-furanboronic acid.

10-5: N-(5-(4-(cyclohexyl)-phenyl)-3-phenyl-2-penten-4-yn-1-yl)-sarcosine tButyl Ester Prepare in a similar fashion from S and cyclohexylboronic acid.

10-6: N-(5-(4-(cyclopentyl)-phenyl)-3-phenyl-2-penten-4-yn-1-yl)-sarcosine tButyl Ester Prepare in a similar fashion from S and cyclopentylboronic acid.

Example 11-1

N-(5-(4-(3furyl)phenyl)-3-phenyl-2-penten-4yn-1-yl)-sarcosine, (H')

The ester G' (2.62 g, 6.13 mmol) was dissolved in 96% formic acid (26 mL). The solution was warmed at 40° C. overnight, then concentrated. Column chromatography (0–8% MeOH/CH$_2$Cl$_2$) provided a pale yellow solid. Trituration with MeOH provided pure H' (0.78 g, 34%) as a white solid. Conversion of 11-1 to the corresponding sodium salt was achieved by suspending 11-1 in methanol and adding 1 equivalent of 6M sodium hydroxide. The solution was then concentrated and the residue was triturated with isopropanol to provide a white solid.

In a similar fashion the following compounds were made from the corresponding intermediate treated under the conditions described above:

11-2: N-(5-(4-(3-thiophene)phenyl)-3-phenyl-2-penten-4-yn-1-yl)-sarcosine, (H')

Prepared in a similar fashion from intermediate 10-2 to provide 11.7 mg (59%) of an off-white solid.

11-3: N-(5-(4-(4-Methyl-3-thiophene)phenyl)-3-phenyl-2-penten-4-yn-1-yl)-sarcosine Prepare in a similar fashion from 10-3.

11-4: N-(5-(4-(4-Methyl-3-furyl)phenyl)-3-phenyl-2-penten-4-yn-1-yl)-sarcosine

Prepare in a similar fashion from 10-4.

11-5: N-(5-(4-(cyclohexyl)-phenyl)-3-phenyl-2-penten-4-yn-1-yl)-sarcosine

Prepare in a similar fashion from 10-5.

10-6: N-(5-(4-(cyclopentyl)-phenyl)-3-phenyl-2-penten-4-yn-1-yl)-sarcosine

Prepare in a similar fashion from 10-6.

Example 12-1

Ethyl 4-(trifluoromethyl)phenylpropiolate (A)

To a solution of 4-iodobenzotrifluoride (256 mg, 0.941 mmol) in triethylamine (2.5 mL) was added ethyl propiolate (0.124 mL, 120 mg, 1.22 mmol), Pd(PPh$_3$)$_4$ (109 mg, 0.0941 mmol), and CuI (54 mg, 0.282 mmol). After 24 hours the reaction mixture was concentrated. Column chromatography (10% EtOAc/hexanes) provided 12-1(149 mg, 65%) as a colourless oil.

In a similar fashion the following compounds were prepared from the corresponding aryliodide and 1.3 equivalents of ethylpropiolate treated under the conditions described above:

12-2: Ethyl 4-fluorophenylpropiolate (A)

Prepared in a similar fashion from 4-fluoroiodobenzene to provide 33 mg (4%) of a colourless solid.

12-3: Ethyl 2-fluorophenylpropiolate (A)

Prepared in a similar fashion from 2-fluoroiodobenzene to provide 3.46 g (93%) of a colourless oil.

12-4: Ethyl 4-chlorophenylpropiolate (A)

Prepared in a similar fashion from 4-chloroiodobenzene to provide 4.60 g (100%) of a colourless solid.

12-5: Ethyl 2-chlorophenylpropiolate (A)

Prepared in a similar fashion from 2-chloroiodobenzene to provide 7.64 g (100%) of a yellow liquid.

12-6: Ethyl 3-thienylpropiolate (A)

Prepared in a similar fashion from 3-thieniliodobenzene to provide 90 mg (53%/o) of a yellow solid.

12-7: Ethyl 4-methoxyphenylpropiolate (A)

Prepared in a similar fashion from 4-methoxyiodobenzene to provide 117 mg (13%) of a colourless oil.

Example 13-1

1-Ethoxycarbonyl-2-(4-(trifluoromethyl)phenyl)-4-trimethylsilyl-1-buten-4-yne (C)

To a solution of Pd(OAc)2 (2.6 mg, 0.0115 mmol) in PhMe (2 mL) was added tris(2,6-dimethoxyphenyl)phosphine (5.1 mg, 0.0115 mmol). After 15 minutes a solution of 12-1 (117 mg, 0.573 mmol) in PhMe (3 mL) was added. After 5 minutes (trimethylsilyl)acetylene (0.081 mL, 56 mg, 0.573 mmol) was added. After 21 hours the reaction mixture was concentrated. Column chromatography (10% EtOAc/hexanes) provided 13-1 (144 mg, 83%) as a yellow oil.

In a similar fashion the following compounds were prepared from the corresponding propiolate intermediate treated by the conditions described above:

13-2: 1-Ethoxycarbonyl-2-(4-fluorophenyl)-4-trimethylsilyl-1-buten-4-yne (C)

Prepared in a similar fashion from intermediate 12-2 to provide 29 mg (58%) of a yellow oil.

13-3: 1-Ethoxycarbonyl-2-(2-fluorophenyl)-4-trimethylsilyl-1-buten-4-yne (C)

Prepared in a similar fashion from intermediate 12-3 to provide 4.19 g (80%) of a yellow oil.

13-4: 1-Ethoxycarbonyl-2-(4-chlorophenyl)-4-trimethylsilyl-1-buten-4-yne (C)

Prepared in a similar fashion from intermediate 12-4 to provide 4.04 g (60%) of a brown oil.

13-5: 1-Ethoxycarbonyl-2-(2-chlorophenyl)-4-trimethylsilyl-1-buten-4-yne (C)

Prepared in a similar fashion from intermediate 12-5 to provide 10.4 g (93%) of a brown oil.

13-6: 1-Ethoxycarbonyl-2-(3-fluorophenyl)-4-trimethylsilyl-1-buten-4-yne (C)

Prepared in a similar fashion from the commercially available intermediate Ethyl 3-fluorophenylpropiolate to provide 0.73 g (85%) of a yellow oil.

13-7: 1-Ethoxycarbonyl-2-(3-thienyl)-4-trimethylsilyl-1-buten-4-yne (C)

Prepared in a similar fashion from intermediate 12-6 to provide 123 mg (90%) of a yellow oil.

13-8: 1-Ethoxycarbonyl-2-(4-methoxyphenyl)-4-trimethylsilyl-1-buten-4-yne (C)

Prepared in a similar fashion from intermediate 12-7 to provide 144 mg (83%) of a yellow oil.

Example 14-1

1-Hydroxy-3-(4-(trifluoromethyl)phenyl)-5-trimethylsilyl-2-penten-4-yne

A solution of 13-1 (144 mg, 0.476 mmol) in anhydrous PhMe (2 mL) was chilled in a dry-ice/acetone bath. A 1.0 M solution of DIBAL-H in PhMe (1.2 mL, 1.19 mmol) was added dropwise. After 5 minutes the chilling bath was removed. After an additional 15 minutes the reaction mixture was chilled in an ice bath and Celite and Na$_2$SO4●10H$_2$O were added to quench the reaction. The reaction mixture was filtered through Celite. The filtrate was concentrated. Column chromatography (20% EtOAc/hexanes) provided 14-1 (114 mg, 92%) as a yellow oil.

In a similar fashion the following compounds were prepared form the corresponding ester intermediates under the conditions described above:

14-2: 1-Hydroxy-3-(4-fluorophenyl)-5-trimethylsilyl-2-penten-4-yne

Prepared in a similar fashion from intermediate 13-2 to provide 19 mg (80%) of a colourless oil.

14-3: 1-Hydroxy-3-(2-fluorophenyl)-5-trimethylsilyl-2-penten-4-yne

Prepared in a similar fashion from intermediate 13-3 to provide 2.65 g (74%) of a yellow oil.

14-4: 1-Hydroxy-3-(4-chlorophenyl)-5-trimethylsilyl-2-penten-4-yne

Prepared in a similar fashion from intermediate 13-4 to provide 2.16 g (62%) of a yellow oil.

14-5: 1-Hydroxy-3-(2-chlorophenyl)-5-trimethylsilyl-2-penten-4-yne

Prepared in a similar fashion from intermediate 13-5 to provide 4.86 g (54%) of a yellow oil.

14-6: 1-Hydroxy-3-(3-fluorophenyl)-5-trimethylsilyl-2-penten-4-yne

Prepared in a similar fashion from intermediate 13-6 to provide 0.47 g (74%) of a pale yellow oil.

14-7: 1-Hydroxy-3-(3-thienyl)-5-trimethylsilyl-2-penten-4-yne

Prepared in a similar fashion from intermediate 13-7 to provide 56 mg (77%) of a yellow oil.

14-8: 1-Hydroxy-3-(4-methoxyphenyl)-5-trimethylsilyl-2-penten-4-yne

Prepared in a similar fashion from intermediate 13-8 to provide 114 mg (92%) of a yellow oil.

Example 15-1

N-(3-(4-(Trifluoromethyl)phenyl)-5-(trimethylsilyl)-2-penten-4-yn-1-yl)-sarcosine, $^t$butyl ester (E)

A solution of 14-1 (115 mg, 0.385 mmol) in anhydrous $CH_2Cl_2$ (4 mL) was chilled in a dry-ice/acetonitrile bath. $PPh_3$ (152 mg, 0.578 mmol) and NBS (103 mg, 0.578 mmol) were added. After 40 minutes saturated $NaHCO_3$ was added. The reaction mixture was partitioned between $CH_2Cl_2$ and saturated $NaHCO_3$. The organic phase was washed with brine, dried ($Na_2SO_4$), filtered, and concentrated to provide crude intermediate D (1-Bromo-3-(4-(trifluoromethyl)phenyl)-5-trimethylsilyl-2-penten-4-yne) used directly in the next step.

To a solution of the crude bromide D (139 mg, 0.385 mmol) in anhydrous MeCN (4 mL) was added t-butyl sarcosine hydrochloride (77 mg, 0.424 mmol), $K_2CO_3$ (532 mg, 3.85 mmol), and KI (320 mg, 1.92 mmol). After 24 hours the reaction mixture was poured into water and extracted with EtOAc. The organic phase was washed with water and brine, dried ($Na_2SO_4$), filtered, and concentrated. Column chromatography (15% EtOAc/hexanes) provided 15-1 (62 mg, 38% over 2 steps) as a colourless oil.

In a similar fashion the following compounds were prepared from the corresponding crude bromide treated under the conditions described above:

15-2: N-(3-(4-fluorophenyl)-5-(trimethylsilyl)-2-penten-4-yn-1-yl)-sarcosine, $^t$butyl ester (E)

Prepared in a similar fashion from intermediate 14-2 to provide 18 mg (63% over 2 steps) of a colourless oil.

15-3: N-(3-(2-fluorophenyl)-5-(trimethylsilyl)-2-penten-4-yn-1-yl)-sarcosine, $^t$butyl ester (E)

Prepared in a similar fashion from intermediate 14-3 to provide 3.24 g (81% over 2 steps) of a yellow oil.

15-4: N-(3-(4-chlorophenyl)-5-(trimethylsilyl)-2-penten-4-yn-1-yl)-sarcosine, $^t$butyl ester (E)

Prepared in a similar fashion from intermediate 14-4 to provide 1.55 g (49%) of a yellow oil.

15-5: N-(3-(2-chlorophenyl)-5-(trimethylsilyl)-2-penten-4-yn-1-yl)-sarcosine, $^t$butyl ester (E)

Prepared in a similar fashion from intermediate 14-5 to provide 5.39 g (75%) of a pale yellow oil.

15-6: N-(3-(3-fluorophenyl)-5-(trimethylsilyi)-2-penten-4-yn-1-yl)-sarcosine, $^t$butyl ester (E)

Prepared in a similar fashion from intermediate 14-6 to provide 0.63 g (89%) of a yellow oil.

15-7: N-(3-(3-thienyl)-5-(trimethylsilyl)-2-penten-4-yn-1-yl)-sarcosine, $^t$butyl ester (E)

Prepared in a similar fashion from intermediate 14-7 to provide 61 mg (71%) of a yellow oil.

15-8: N-(3-(4-methoxyphenyl)-5-(trimethylsilyl)-2-penten-4-yn-1-yl)-sarcosine, $^t$butyl ester (E)

Prepared in a similar fashion from intermediate 14-8 to provide 14 mg (10%) of a yellow oil.

Example 16-1

N-(3-(4-(Trifluoromethyl)phenyl)-2-penten-4-yn-1-yl)sarcosine, $^t$butyl ester (F)

To a solution of 15-1 (62 mg, 0.146 mmol) in MeOH (2 mL) was added $K_2CO_3$ (101 mg, 0.730 mmol). After 15 minutes the reaction mixture was poured into water and extracted with EtOAc. The organic phase was washed with brine, dried ($MgSO_4$), filtered, and concentrated to provide 16-1 (36 mg, 71%) as a yellow oil.

In a similar fashion the following compounds were prepared from the corresponding trimethylsilyl intermediates under the conditions described above:

16-2: N-(3-(4-fluorophenyl)-2-penten-4-yn-1-yl)sarcosine, $^t$butyl ester (F)

Prepared in a similar fashion from intermediate 15-2 to provide 13 mg (93%) of a yellow oil.

16-3: N-(3-(2-fluorophenyl)-2-penten-4-yn-1-yl)sarcosine, $^t$butyl ester (F)

Prepared in a similar fashion from intermediate 15-3 to provide 2.22 g (85%) of a colourless oil.

16-4: N-(3-(4-chlorophenyl)-2-penten-4-yn-1-yl)sarcosine, $^t$butyl ester (F)

Prepared in a similar fashion from intermediate 15-4 to provide 0.80 g (76%) of a yellow oil.

16-5: N-(3-(2-chlorophenyl)-2-penten-4-yn-1-yl)sarcosine, $^t$butyl ester (F)

Prepared in a similar fashion from intermediate 15-5 to provide 3.72 g (85%) of a yellow oil.

16-6: N-(3-(3-fluorophenyl)-2-penten-4-yn-1-yl)sarcosine, $^t$butyl ester (F)

Prepared in a similar fashion from intermediate 15-6 to provide 0.42 g (83%) of a pale yellow solid.

16-7: N-(3-(3-thienyl)-2-penten-4-yn-1-yl)sarcosine, $^t$butyl ester (F)

Prepared in a similar fashion from intermediate 15-7 to provide 46 mg (96%) of a yellow solid.

16-8: N-(3-(4-methoxyphenyl)-2-penten-4-yn-1-yl)
sarcosine, 'butyl ester (F)

Prepared in a similar fashion from intermediate 15-8 to provide 15 mg (I 36%) of a yellow oil.

Example 17-1

N-(5-(4-Isopropylphenyl)-3-(4-(trifluoromethyl)
phenyl)-2-penten-4-yn-1-yl)-sarcosine, butyl ester
(G)

To a solution of 16-1 (35 mg, 0.099 mmol) in triethylamine (2 mL) was added 4-iodoisopropylbenzene (32 mg, 0.129 mmol), Pd(PPh$_3$)$_4$ (11 mg, 0.0099 mmol), and CuI (5.5 mg, 0.029 mmol). After 18 hours the reaction mixture was concentrated. Column chromatography (10% EtOAc/hexanes) provided 17-1 (40 mg, 86%) as a colourless oil.

In a similar fashion the following compounds were prepared from 1.3 equivalents of the appropriate aryliodide with the corresponding alkyne intermediate according to the conditions described above:

17-2: N-(5-(4-Isopropylphenyl)-3-(4-fluorophenyl)-
2-penten-4yn-1-yl)-sarcosine, 'butyl ester (G)

Prepared in a similar fashion from intermediate 16-2 and 4-isopropyliodobenzene to provide 14 mg (76%) of a colourless oil.

17-3: N-(5-(4-Isopropylphenyl)-3-(2-fluorophenyl)-
2-penten-4-yn-1-yl)-sarcosine, 'butyl ester (G)

Prepared in a similar fashion from intermediate 16-3 and 4-isopropyliodobenzene to provide 440 mg (79%) of a yellow oil.

17-4: N-(5-(4-t-Butylphenyl)-3-(2-fluorophenyl)-2-
penten-4-yn-1-yl)-sarcosine, 'butyl ester (G)

Prepared in a similar fashion from intermediate 16-3 and 4-t-butyliodobenzene to provide 500 mg (87%) of a yellow oil.

17-5: N-(5-(4-Isopropylphenyl)-3-(4-chlorophenyl)-
2-penten-4-yn-1-yl)-sarcosine, 'butyl ester (G)

Prepared in a similar fashion from intermediate 16-4 and 4-isopropyliodobenzene to provide 0.50 g (883) of a pale yellow oil.

17-6: N-(5-(4-t-Butylphenyl)-3-(4-chlorophenyl)-2-
penten-4-yn-1-yl)-sarcosine, 'butyl ester (G)

Prepared in a similar fashion from intermediate 16-4 and 4-tbutyliodobenzene to provide 514 mg (83%) of a pale yellow oil.

17-7: N-(5-(4-Isoproylphenyl)-3-(2-chlorophenyl)-2-
penten-4-yn-1-yl)-sarcosine, 'butyl ester (G)

Prepared in a similar fashion from intermediate 16-5 and 4-isopropyliodobenzene to provide 0.53 g (97%) of a yellow oil.

17-9: N-(5-(4-t-Butylphenyl)-3-(2-clorophenyl)-2-
penten-4-yn-1-yl)-sarcosine, 'butyl ester (G)

Prepared in a similar fashion from intermediate 16-5 and 4-t-biutyliodobenzene to provide 0.52 g (92%) of a yellow oil.

17-9: N-(5-(4-Isopropylphenyl)-3-(3-flurophenyl)-2-
penten-4-yn-1-yl)-sarcosine, 'butyl ester (G)

Prepared in a similar fashion from intermediate 16-6 and 4-isopropyliodobenzene to provide 0.16 g (03%) of a yellow oil.

17-10: N-(5-(4-Isopropylphenyl)-3-(3-thienyl)-2-
penten-4-yn-1-yl)-sarcosine, 'butyl ester (G)

Prepared in a similar fashion from intermediate 16-7 and 4-isopropyliodobenzene to provide 54 mg (86%) of a yellow oil.

17-11: N-(5-(4-Isopropylphenyl)-3-(4-
methoxyphenyl)-2-penten-4-yn-1-yl)-sarcosine,
'butyl ester (G)

Prepared in a similar fashion from intermediate 16-8 and 4-isopropyliodobenzene to provide 21 mg (129%) of a colourless oil.

17-12: N-(5-(3,4-Methylenedioxyphenyl)-3-(3-
fluorophenyl)-2-penten-4-yn-1-yl)-sarcosine, 'butyl
ester (G)

Prepared in a similar fashion from intermediate 16-6 and 3,4-methylenedioxyiodobenzene to provide 74.1 mg (106%) of a brown oil.

17-13: N-(5-(4-Ethylphenyl)-3-(2-chlorophenyl)-2-
penten-4-yn-1-yl)-sarcosine, 'butyl ester (G)

Prepared in a similar fashion from intermediate 16-5 and 4-ethyliodobenzene to provide 44.0 mg (110%) of a light yellow oil.

17-4: N-(5-(4-Propylphenyl)-3-(2-chlorophenyl)-2-
penten-4-yn-1-yl)-sarcosine, 'butyl ester (G)

Prepared in a similar fashion from intermediate 16-5 and 4-propyliodobenzene to provide 39.5 mg (96%) of a light yellow oil.

Example 18-1

N-(5-(4-Isopropylphenyl)-3-(4-(trifluoromethyl)
phenyl)-2-penten-4-yn-1-yl)-sarcosine (H)

A solution of 17-1 (40 mg, 0.0849 mmol) in formic acid (2 mL) was warmed at 40° C. for 18 hours. The reaction mixture was concentrated. Column chromatography (0–100% MeOH/CH$_2$Cl$_2$) provided 18-1 (36 mg, 99%) as a yellow oil.

In a similar fashion the following compounds were prepared from the corresponding t-butyl ester intermediate under the conditions described above:

18-2: N-(5-(4-Isopropylphenyl)-3-(4-fluorophenyl)-
2-penten-4-yn-1-yl)-sarcosine (H)

Prepared in a similar fashion from intermediate 17-2 to provide 13 mg (107%) of a colourless oil.

18-3: N-(5-(4-Isopropylphenyl)-3-(2-fluorophenyl)-
2-penten-4-yn-1-yl)-sarcosine (H)

Prepared in a similar fashion from intermediate 17-3 to provide 379 mg (99%) of a pale yellow oil.

18-4: N-(5-(4-t-Butylphenyl)-3-(2-fluorophenyl)-2-
penten-4-yn-1-yl)-sarcosine (H)

Prepared in a similar fashion from intermediate 17-4 to provide 434 mg (100%) of a yellow oil.

18-5: N-(5-(4-Isopropylphenyl)-3-(4-chlorophenyl)-
2-penten-4-yn-1-yl)-sacosine (H)

Prepared in a similar fashion from intermediate 17-5 to provide 436 mg (96%) of a beige solid.

18-6: N-(5-(4-t-Butylphenyl)-3-(4-chlorophenyl)-2-penten-4-yn-1-yl)-sarcosine (H)

Prepared in a similar fashion from intermediate 17-6 to provide 408 mg (88%) of a beige solid.

18-7: N-(5-(4-Isopropylphenyl)-3-(2-chlorophenyl)-2-penten-4-yn-1-yl)-sarcosine (H)

Prepared in a similar fashion from intermediate 17-7 to provide 438 mg (95%) of an off-white foam.

18-8: N-(5-(4-t-Butylphenyl)-3-(2-chlorophenyl)-2-penten-4-yn-1-yl)-sarcosine (H)

Prepared in a similar fashion from intermediate 17-8 to provide 448 mg (97%) of a colourless foam.

18-9: N-(5-(4-Isopropylphenyl)-3-(3-fluorophenyl)-2-penten-4-yn-1-yl)-sarcosine (H)

Prepared in a similar fashion from intermediate 17-9 to provide 0.12 g (93%) of a colourless oil.

18-10: N-(5-(4-Isopropylphenyl)-3-(3-thienyl)-2-penten-4-yn-1-yl)-sarcosine (H)

Prepared in a similar fashion from intermediate 17-10 to provide 34 mg (72%) of a yellow solid.

18-11: N-(5-(4-Isopropylphenyl)-3-(4-methoxyphenyl)-2-penten-4-yn-1-yl)-sarcosine (H)

Prepared in a similar fashion from intermediate 17-11 to provide 14 mg (76%) of a colourless oil.

18-12: N-(5-(3,4-Methylenedioxyphenyl)-3-(3-fluorophenyl)-2-penten-4-yn-1-yl)-sarcosine (H)

Prepared in a similar fashion from intermediate 17-12 to provide 64.1 mg (88%) of a orange-brown oil.

18-13: N-(5-(4-Ethylphenyl)-3-(2-chlorophenyl)-2-penten-4-yn-1-yl)-sarcosine (H)

Prepared in a similar fashion from intermediate 17-13 to provide 30.1 mg (79%) of a colourless oil.

18-14: N-(5-(4-Propylphenyl)-3-(2-chlorophenyl)-2-penten-4-yn-1-yl)-sarcosine (H)

Prepared in a similar fashion from intermediate 17-14 to provide 13.9 mg (40%) of a light yellow oil.

Example 20

Assay of Transport via GlyT-1

This example illustrates a method for the measurement of glycine uptake by transfected cultured cells.

Cells stably transfected with GlyT-1 C (see Kim, et al., *Molecular Pharmacology*, 45, 1994:608–617) were washed twice with HEPES buffered saline (HBS). The cells were then incubated 10 minutes at 37 C., after which a solution was added containing 50 nM [$^3$H]glycine (17.5 Ci/mmol) and either (a) no potential competitor, (b) 10 mM nonradioactive glycine or (c) a concentration of a candidate drug. A range of concentrations of the candidate drug was used to generate data for calculating the concentration resulting in 50% of the effect (e.g., the $IC_{50}$s, which are the concentrations of drug inhibiting glycine uptake by 50%). The cells were then incubated another 10 minutes at 37° C., after which the cells were aspirated and washed three times with ice-cold HBS. The cells were harvested, scintillant was added to the cells, the cells were shaken for 30 minutes, and the radioactivity in the cells was counted using a scintillation counter. Data were compared between the same cells contacted or not contacted by a candidate agent, depending on the assay being conducted.

The compounds of the present invention were active as GlyT-1 inhibitors.

Example 21

Assay of Binding to NMDA Receptors

This example illustrates binding assays to measure interaction of compounds with the glycine site on the NMDA receptor. Direct binding of [$^3$H]glycine to the NMDA-glycine site was performed according to the method of Grimwood et al., *Molecular Pharmacology*, 41, 923–930 (1992); Yoneda et al., *J. Neurochem*, 62, 102–112 (1994).

The binding test was performed in eppendorf tubes containing 150 μg of membrane protein and 50 nM [$^3$H]glycine in a volume of 0.5 ml. Non-specific binding was determined with 1 mM glycine. Drugs were dissolved in assay buffer (50 mM Tris-acetate, pH 7.4) or DMSO (final concentration of 0.1%). Membranes were incubated on ice for 30 minutes and bound radioligand was separated from free radioligand by filtration on Whatman GF/B glass fiber filters or by centrifugation (18,000×g, 20 min). Filters or pellet was washed three times quickly with ice-cold 5 mM Tris-acetate buffer. Filters were dried and placed in scintillation tubes and counted. Pellets were dissolved in deoxycholate/NaOH (0.1 N) solution overnight, neutralized and radioactivity was determined by scintillation counting.

A second binding test for the NMDA-glycine site used [3H]dichlorokynurenic acid (DCKA) and membranes prepared as above. See, Yoneda et al., *J. Neurochem.*, 60,634–645 (1993). The binding assay was performed as described for [$^3$H]glycine above except that [$^3$H]DCKA was used to label the glycine site. The final concentration of [$^3$H]DCKA was 10 nM, and the assay was performed for 10 minutes on ice.

A third binding test used for the NMDA-glycine site used indirect assessment of affinity of ligands for the site by measuring the binding of [3H]MK-801 (dizocilpine). See, Palmer and Burns, *J. Neurochem.*, 62, 187–196 (1994). Preparation of membranes for the test was the same as above. The binding assay allowed separate detection of antagonists and agonists.

The third binding test was operated to identify antagonists as follows: 100 μg of membranes were added to wells of a 96-well plate, along with glutamate (10 μM) and glycine (200 nM) and various concentrations of the ligand to be tested. The assay was started by the addition of 5 nM [$^3$H]MK-801 (23.9 Ci/mmol), which binds to the ion channel associated with NMDA receptors. The final volume of the assay was 200 μl. The assay was performed for 1 hour at room temperature. Bound radioactivity was separated from free by filtration, using a TOMTEC harvester. Antagonist activity was indicated by decreasing radioactivity associated with the NMDA receptor with increasing concentration of the tested ligand.

The third binding test was operated to identify agonists by performing the test as above, except that the concentration of glycine was 200 nM. Agonist activity was indicated by increasing radioactivity associated with the NMDA receptor with increasing concentration of the tested ligand.

What is claimed:
1. A compound of Formula I:

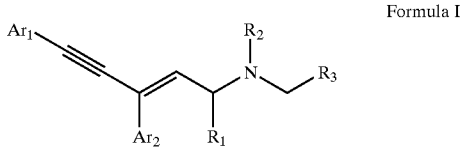

Formula I wherein:
Ar$_1$ and Ar$_2$ are independently selected aryl groups, optionally substituted with up to five substituents independently selected from the group consisting of alkyl, alkoxy, cycloalkyl, cycloalkyloxy, alkanoyl, thioalkyl, aralkyl, aralkyloxy, aryloxyalkyl, aryloxyalkoxy, cycloalkyl-substituted alkyl, cycloalkyloxy-substituted alkyl, cycloalkyl-substituted alkoxy, cycloalkyloxy-substituted alkoxy, thioaryl, aralkylthio, thioaryl-alkyl, aralkylthioalkyl, halo, NO$_2$, CF$_3$, CN, OH, alkylenedioxy, SO$_2$NRR', NRR', CO$_2$R (where R and R' are independently selected from the group consisting of H and alkyl), and a second aryl group, which may be substituted as above, wherein the aryls of the substitutions are carbocyclic;

R$_1$ is selected from the group consisting of H and alkyl;

R$_2$ is selected from the group consisting of H, alkyl and benzyl;

R$_3$ is selected from the group consisting of CO$_2$R, CONRR', CONH(OH), COSR, SO$_2$NRR', PO(OR)(OR') and tetrazolyl, wherein R and R' are independently selected from the group consisting of H and alkyl;

and a salt, solvate or hydrate thereof.

2. A compound according to claim 1, wherein Ar$_1$ is an aryl group, optionally substituted with up to three substituents independently selected from halo, NO$_2$, CF3, CN, OH, SO$_2$NRR', NRR', CO$_2$R (where R and R' are independently selected from the group consisting of H and alkyl), and a substituent of the formula R''—(X)n— wherein n is 0 or 1;

X is CH$_2$ or a heteroatom;

R'' is H, alkyl and aryl substituted optionally with up to three substituents selected from alkyl, halo, NO$_2$, CF$_3$, CN, OH, SO$_2$NRR', NRR' and CO$_2$R, wherein R and R' are independently selected from the group consisting of H and alkyl.

3. A compound according to claim 2, wherein Ar$_1$ is phenyl.

4. A compound according to claim 2, wherein Ar$_1$ is substituted phenyl.

5. A compound according to claim 4, wherein Ar$_1$ is lower alkyl substituted phenyl.

6. A compound according to claim 5, wherein Ar$_1$ is 4-(alkyl)-phenyl.

7. A compound according to claim 6, wherein said alkyl group is selected from methyl, ethyl, n-propyl, isopropyl and n-butyl.

8. A compound according to claim 1, wherein Ar$_1$ is alkylenedioxyphenyl.

9. A compound according to claim 8, wherein Ar$_1$ is methylendioxyphenyl.

10. A compound according to claim 9, wherein Ar$_1$ is 3,4-methylenedioxyphenyl.

11. A compound according to claim 1, wherein Ar$_1$ is a benzo-fused aromatic group.

12. A compound according to claim 11, wherein Ar$_1$ is carbocyclic.

13. A compound according to claim 12, wherein Ar$_1$ is naphthyl.

14. A compound according to claim 13, wherein Ar$_1$ is 2-naphthyl.

15. A compound according to claim 1, wherein Ar$_2$ is an aryl group optionally substituted with up to three substituents independently selected from halo, haloalkyl, alkyl, haloalkoxy, and alkoxy.

16. A compound according to claim 15 in which Ar$_2$ is unsubstituted aryl.

17. A compound according to claim 16 in which Ar$_2$ is phenyl.

18. A compound according to claim 15, wherein Ar$_2$ is substituted phenyl.

19. A compound according to claim 18, wherein Ar$_2$ is halo-substituted phenyl.

20. A compound according to claim 19, wherein Ar$_2$ is phenyl substituted by chloro or fluoro.

21. A compound according to claim 1, wherein R$_1$ is H.

22. A compound according to claim 1, wherein R$_2$ is H.

23. A compound according to claim 22, wherein R$_3$ is methyl.

24. A compound according to claim 1, wherein R$_3$ is COOR.

25. A compound according to claim 24, wherein R$_3$ is COOH.

26. A compound according to claim 1, selected from:
N-(5-(4-Fluorophenyl)-3-phenyl-2-penten-4-yn-1-yl)-sarcosine
N-(5-(2-Fluorophenyl)-3-phenyl-2-penten-4-yn-1-yl)-sarcosine
N-(5-(2,4-Difluorophenyl)-3-phenyl-2-penten-4-yn-1-yl)-sarcosine
N-(5-(3-Nitrophenyl)-3-phenyl-2-penten-4-yn-1-yl)-sarcosine
N-(5-(4-Nitrophenyl)-3-phenyl-2-penten-4-yn-1-yl)-sarcosine
N-(3-Phenyl-5-(2-thiomethylphenyl)-2-penten-4-yn-1-yl)-sarcosine
N-(5-(4-Chlorophenyl)-3-phenyl-2-penten-4-yn-1-yl)-sarcosine
N-(5-(4-Isopropylphenyl)-3-phenyl-2-penten-4-yn-1-yl)-sarcosine,
N-(5-(3,5-Bis(trifluoromethyl)phenyl)-3-phenyl-2-penten-4-yn-1-yl)-sarcosine
N-(3,5-Diphenyl-2-penten-4-yn-1-yl)-sarcosine
N-(5-(4-diphenyl)-3-phenyl-2-penten-4-yn-1-yl)-sarcosine
N-(5-(4-trifluoromethylphenyl)-3-phenyl-2-penten-4-yn-1-yl)-sarcosine
N-(5-(4-benzylphenyl)-3-phenyl-2-penten-4-yn-1-yl)-sarcosine
N-(5-(4-ethylphenyl)-3-phenyl-2-penten-4-yn-1-yl)-sarcosine
N-(5-(4-npropylphenyl)-3-phenyl-2-penten-4-yn-1-yl)-sarcosine
N-(5-(4-nbutylphenyl)-3-phenyl-2-penten-4-yn-1-yl)-sarcosine
N-(5-(4-npentylphenyl)-3-phenyl-2-penten-4-yn-1-yl)-sarcosine
N-(5-(4-phenoxyphenyl)-3-phenyl-2-penten-4-yn-1-yl)-sarcosine
N-(5-(1-naphthyl)-3-phenyl-2-penten-4-yn-1-yl)-sarcosine
N-(5-(4-methylphenyl)-3-phenyl-2-penten-4-yn-1-yl)-sarcosine
N-(5-(3-isopropylphenyl)-3-phenyl-2-penten-4-yn-1-yl)-sarcosine N-(5-(2-naphthyl)-3-phenyl-2-penten-4-yn-1-yl)-sarcosine
N-(5-(3,4-dimethylphenyl)-3-phenyl-2-penten-4-yn-1-yl)-sarcosine
N-(5-(2-isopropylphenyl)-3-phenyl-2-penten4-yn-1-yl)-sarcosine
N-(5-(3,4-methylenedioxyphenyl)-3-phenyl-2-penten-4-yn-1-yl)-sarcosine
N-(5-(4-trifluoromethoxyphenyl)-3-phenyl-2-penten-4-yn-1-yl)-sarcosine
N-(5-(3,4-dimethoxyphenyl)-3-phenyl-2-penten-4-yn-1-yl)-sarcosine
N-(3-Phenyl-5-(4-thiomethylphenyl)-2-penten-4-yn-1-yl)-sarcosine
N-(5-(4-Methylphenyl)-3-phenyl-2-penten-4-yn-1-yl)-sarcosine
N-(3-Phenyl-5-(4-t-butylphenyl)-2-penten-4-yn-1-yl)-sarcosine
N-(5-(4-Isopropylphenyl)-3-(4-(trifluoromethyl)phenyl)-2-penten-4-yn-1-yl)-sarcosine
N-(5-(4-Isopropylphenyl)-3-(4-fluorophenyl)-2-penten-4-yn-1-yl)-sarcosine
N-(5-(4-Isopropylphenyl)-3-(2-fluorophenyl)-2-penten-4-yn-1-yl)-sarcosine
N-(5-(4-t-Butylphenyl)-3-(2-fluorophenyl)-2-penten-4-yn-1-yl)-sarcosine
N-(5-(4-Isopropylphenyl)-3-(4-chlorophenyl)-2-penten-4-yn-1-yl)-sarcosine
N-(5-(4-t-Butylphenyl)-3-(4-chlorophenyl)-2-penten-4-yn-1-yl)-sarcosine
N-(5-(4-Isopropylphenyl)-3-(2-chlorophenyl)-2-penten-4-yn-1-yl)-sarcosine
N-(5-(4-t-Butylphenyl)-3-(2-chlorophenyl)-2-penten-4-yn-1-yl)-sarcosine
N-(5-(4-Isopropylphenyl)-3-(3-fluorophenyl)-2-penten-4-yn-1-yl)-sarcosine
N-(5-(4-Isopropylphenyl)-3-(4-methoxyphenyl)-2-penten-4-yn-1-yl)-sarcosine
N-(5-(3,4-Methylenedioxyphenyl)-3-(3-fluorophenyl)-2-penten-4-yn-1-yl)-sarcosine
N-(5-(4-Ethylphenyl)-3-(2-chlorophenyl)-2-penten-4-yn-1-yl)-sarcosine, and
N-(5-(4-Propylphenyl)-3-(2-chlorophenyl)-2-penten-4-yn-1-yl)-sarcosine.

27. A pharmaceutical composition comprising a therapeutically effective amount of a compound according to claim 1, and a pharmaceutically acceptable carrier.

28. A method for treating a patient having a medical condition for which a glycine transport inhibitor is indicated, comprising the step of ministering to the patient a pharmaceutical composition as defined in claim 27.

29. A method according to claim 28 in which the medical condition is schizophrenia.

30. A method according to claim 28 in which the medical condition is cognitive dysfunction.

31. A method according to claim 28 in which the medical condition is Alzheimer's disease.

* * * * *